(12) United States Patent
Yung et al.

(10) Patent No.: US 7,491,367 B2
(45) Date of Patent: *Feb. 17, 2009

(54) SYSTEM AND METHOD FOR PROVIDING A STANDARDIZED STATE INTERFACE FOR INSTRUMENTATION

(75) Inventors: Kai Yung, Livermore, CA (US); Sylvia H. Fang, Fremont, CA (US)

(73) Assignee: Applera Corporation, Foster City, CA (US)

( * ) Notice: Subject to any disclaimer, the term of this patent is extended or adjusted under 35 U.S.C. 154(b) by 759 days.

This patent is subject to a terminal disclaimer.

(21) Appl. No.: 10/454,759

(22) Filed: Jun. 4, 2003

(65) Prior Publication Data

US 2004/0039531 A1 Feb. 26, 2004

Related U.S. Application Data

(60) Provisional application No. 60/411,574, filed on Sep. 16, 2002, provisional application No. 60/386,296, filed on Jun. 4, 2002.

(51) Int. Cl.
*F01N 3/20* (2006.01)

(52) U.S. Cl. .................... 422/105; 422/62; 422/107; 422/129; 422/130; 422/134; 702/19; 702/22; 702/30; 702/31

(58) Field of Classification Search .......... 422/99, 422/105, 107, 119, 129, 130, 131, 62, 102, 422/134; 700/108, 109, 266, 267, 268, 269; 702/22, 23, 27, 29, 30, 31, 32, 81–84, 19
See application file for complete search history.

(56) References Cited

U.S. PATENT DOCUMENTS 5,029,065 A 7/1991 Nau et al.
5,594,858 A 1/1997 Blevins
5,619,685 A 4/1997 Schiavone
5,841,975 A 11/1998 Layne et al.
6,202,153 B1 3/2001 Diamant et al.
6,507,945 B1 * 1/2003 Rust et al. .................. 717/103
6,689,324 B2 * 2/2004 Inoue ........................ 422/130

(Continued)

FOREIGN PATENT DOCUMENTS

EP 0 596 205 8/1993

(Continued)

OTHER PUBLICATIONS

International Search Report for PCT/US2003/017940.

*Primary Examiner*—Jill Warden
*Assistant Examiner*—Dwayne K Handy
(74) *Attorney, Agent, or Firm*—Knobbe, Martens, Olson & Bear, LLP

(57) ABSTRACT

An instrumentation interface that provides a standardized states of a plurality of devices to a control system. Coordinating the operation of the plurality of devices in an analytical system is simplified by allowing the control system to perform in terms of simplified standard states. Device specific states that vary for different types of devices are logically linked to the standardized states via a form of a translator. By having the control system not worry about the specifics of a device, its ability to coordinate large number of devices is improved.

25 Claims, 26 Drawing Sheets

U.S. PATENT DOCUMENTS

| | | | |
|---|---|---|---|
| 6,727,096 B1 * | 4/2004 | Wang et al. | 436/37 |
| 6,824,742 B1 * | 11/2004 | Inoue | 422/116 |
| 6,909,974 B2 * | 6/2005 | Yung et al. | 702/31 |
| 6,944,522 B2 * | 9/2005 | Karmiy et al. | 700/273 |
| 6,983,227 B1 | 1/2006 | Thalhammer-Reyero | |
| 6,990,221 B2 * | 1/2006 | Shams | 382/129 |
| 2002/0013832 A1 | 1/2002 | Hubbard | |
| 2003/0055835 A1 | 3/2003 | Roth | |
| 2004/0012633 A1 | 1/2004 | Helt | |
| 2004/0030504 A1 | 2/2004 | Helt et al. | |
| 2004/0032430 A1 | 2/2004 | Yung et al. | |
| 2004/0034478 A1 | 2/2004 | Yung et al. | |
| 2004/0042471 A1 | 3/2004 | Yung et al. | |
| 2005/0106736 A1 | 5/2005 | Yung et al. | |
| 2007/0129894 A1 | 6/2007 | Yung et al. | |

FOREIGN PATENT DOCUMENTS

| | | |
|---|---|---|
| WO | WO 99/27427 | 11/1998 |
| WO | WO 01/59406 | 8/2001 |
| WO | WO 01/90951 | 11/2001 |

* cited by examiner

| Device | If in INITIALIZE state | If in STANDBY state | If in TASK state | If in COMPLETED state | If in FAULT state |
|---|---|---|---|---|---|
| System monitor | Initialize if not initialized | Continue standby | Continue system monitoring | N/A | Halt system |
| Sample storage | Initialize if not initialized | Continue standby | Continue sample storage | Change Robotics to TASK | Attempt to recover or exit gracefully |
| Sample transfer | Initialize if not initialized | Continue standby | Continue sample transport | Change Multiplexer to TASK | Attempt to recover or exit gracefully |
| Sample multiplexer | Initialize if not initialized | Continue standby | Continue sample multiplexing | Change Analyzer to TASK | Attempt to recover or exit gracefully |
| Sample analyzer | Initialize if not initialized | Continue standby | Continue sample analysis | Change Data processor to TASK | Attempt to recover or exit gracefully |
| Data processor | Initialize if not initialized | Continue standby | Continue data processing | Halt system | Attempt to recover or exit gracefully |

FIG. 6

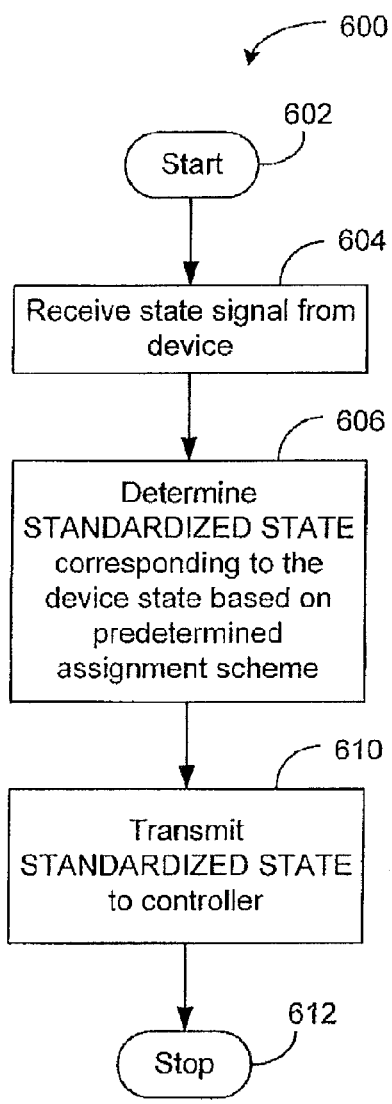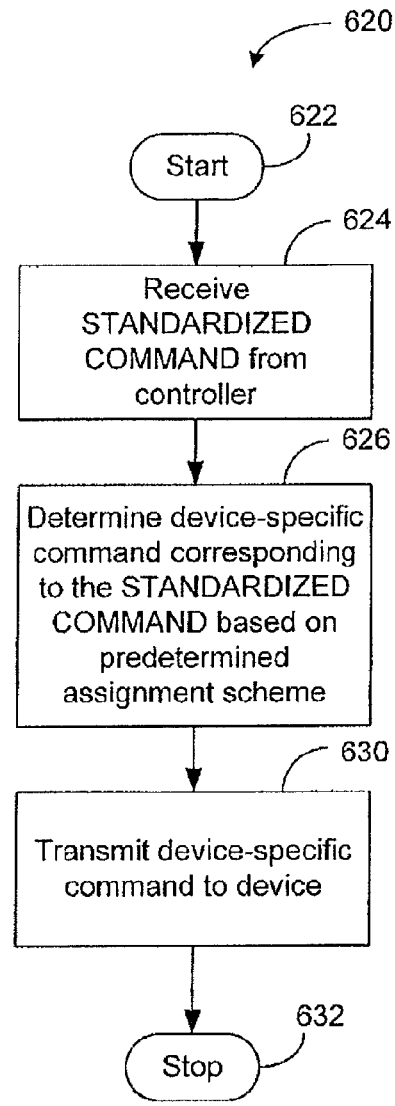
FIG. 7B
FIG. 7C

| Exemplary translation for sample storage | |
|---|---|
| Device-specific states to STANDARDIZED STATES | STANDARDIZED COMMANDS to device-specific commands |
| If "idle," "nominal temperature," "ready," or "standby," then STANDBY.<br><br>If "locate sample," "retrieve sample," "make sample accessible to robotics," end of dispensing," or "dispensing," then TASK.<br><br>If "non-nominal temperature," "attempt nominal temperature," "storage temperature fault," "dispensing error," "error recovery," "dispensing fault," or "fault," then FAULT.<br><br>If "completed," then COMPLETED. | If STANDBY command,<br>  - if device not in "standby" state, then go to "standby" state<br>  - if device already in "standby" state, then continue standby operation<br><br>If TASK command,<br>  - if device not in "dispensing" state, then go to "dispensing" state<br>  - if device already in "dispensing" state, then continue dispensing operation<br><br>If FAULT command,<br>  - if device not in "fault" state, then<br>    - if device in "dispensing" state and dispensing operation not affected by FAULT, then remain in "dispensing" state<br>    - if device in "dispensing" state and dispensing operation affected by FAULT, then go to "standby" state<br>    - if device in "standby" state, then remain in "standby" state<br>  - if device is already in "fault" state, then continue fault handling process<br><br>If COMPLETED command, then remain "completed" |

FIG. 9B

SYSTEM AND METHOD FOR PROVIDING A STANDARDIZED STATE INTERFACE FOR INSTRUMENTATION

CLAIM OF PRIORITY

This U.S. patent application claims priority to U.S. Provisional Patent Application No. 60/386,296 entitled "Informatics System Architecture" filed Jun. 4, 2002 and U.S. Provisional Patent Application No. 60/411,574 entitled "Integration Instructions For Informatics System Architecture" filed Sep. 16, 2002 which are hereby incorporated by reference. Additionally, this application relates to the following applications filed on the same date which are hereby incorporated by reference in their entirety: Ser. No. 10/455,262 entitled "System And Method For Open Control And Monitoring Of Biological Instruments", Ser. No. 10/455,264 entitled "System And Method For Discovery Of Biological Instruments", and Ser. No. 10/455,263 entitled "System And Method For Generating User Interfaces For Different Instrument Types".

BACKGROUND

1. Field

The present teachings generally relate to methods and system useful for controlling a plurality of devices that make up a biological analytical system and more particularly to a method and system for controlling the devices by providing interfaces that allow standardizing the manner in which states of the devices are represented in the controlling scheme.

2. Description of the Related Art

A DNA-related analysis laboratory is an example of a biological analysis laboratory that may include a large number of analytical devices. The devices can either prepare samples, measure samples, or process data from the measurements. In a typical DNA-related analysis, it may be desirable to perform different types of analytical measurements to yield various aspects of the desired result.

Because different types of analytical devices operate inherently differently, controlling and coordinating large numbers of such devices typically requires substantial amount of human intervention. Such human attention may be required during some portion of an analysis chain because the various devices are not sufficiently integrated. Human attention may also be required when integrating different devices into an existing system, because one may need to reconfigure the configuration of a control system so that it recognizes the new device. While such operator-intensive approach may be suitable in small scale systems, it is a substantial concern in larger systems.

SUMMARY

The aforementioned needs are satisfied by various aspects of the present teachings. One aspect of the present teachings relates to a system for controlling the operation of a biological laboratory having a plurality of biological processing devices. The at least some of the biological processing devices have interrelated operational dependence. The system comprises a control system that monitors and controls the operation of the plurality of biological processing devices. The control system includes a standardized state logic having a plurality of standardized commands and an interrelationship database that correlates the interrelationship between a change of state of one of the biological processing devices to another of the biological processing devices. The control system, in response to receiving a state change from a first biological processing device determines a desired state of a second biological processing device from the interrelationship database and sends a standardized state change command to the second biological device. The system further comprises a plurality of translation components associated with the plurality of biological processing devices. The plurality of translation components includes a customized instruction set that instructs the biological processing device to change from a first state to a second state in response to receiving the standardized state change command from the control system. The plurality of translation components include at least one sample analyzer translation component for at least one sample analyzer. The at least one sample analyzer translation component receives standardized commands from the control system such that the at least one sample analyzer is instructed by the at least one sample analyzer translation component to obtain identification information about the biological sample.

In certain embodiments, the standardized state diagram comprises a normal state and a fault state. The standardized normal and fault states for a given devices represent functionally similar device-specific normal and fault states. The normal state of the standardized state diagram comprises a task state and a standby state. The normal state of the-standardized state diagram further comprises a completed state. The control system, upon receiving the standardized completed state from the first device, determines the second device's state in response to the first device's state. The control system instructs the second device to go into the task state if it is in the standby state.

In certain embodiments, the plurality of biological processing devices includes a sample storage device. In other embodiments, the plurality of biological processing devices includes a sample transfer device. The sample transfer device comprises a robotics device. In other embodiments, the plurality of biological processing devices includes a sample multiplexing device. The multiplexing device comprises a thermalcycler device. In other embodiments, the plurality of biological processing devices includes the at least one sample analyzer such as a mass spectrometer, a DNA sequencing device, an electrophoresis device, and an array device. In other embodiments, the plurality of biological processing devices includes a system monitoring device that monitors the operating conditions of the biological laboratory.

In certain embodiments, the translation component for a given biological processing device is functionally located in a front end component of the given device. In other embodiments, the translation component for a given biological processing device is functionally located in a translation repository accessible by the control system and the given biological processing device.

Another aspect of the present teachings relates to a method of controlling the operation of a plurality of biological processing devices adapted to facilitate biological assays. The method comprises monitoring the states of the plurality of biological processing devices in a standardized format. The standardized states of the plurality of biological processing devices are obtained from device-specific states of the plurality of biological processing devices by transforming the device-specific states into the standardized format. The method further comprises determining a course of action representative of an interrelated functioning of the plurality of biological processing devices based at least in part on the monitored standardized states of the plurality of biological processing devices. The method further comprises transmitting a set of standardized commands representative of the course of action to the plurality of biological processing devices. The standardized commands are transformed into formats recognizable by the plurality of biological processing devices.

In certain embodiments, monitoring the states of the plurality of biological processing devices comprises monitoring to see if the devices are in a standardized normal state or a standardized fault state. The normal state comprises a task state and a standby state. The normal state further comprises a completed state. Determining a course of action comprises receiving the completed state of a first device and in response, determining that a second device's state is to be changed based on the first device's completed state. The second device's state is to be changed to the task state if it is in the standby state.

In certain embodiments, transmitting the standardized commands to a given device comprises transforming the standardized commands to the device-specific commands at a front end component of the given device. In other embodiments, transmitting the standardized commands to a given device comprises transforming the standardized commands to the device-specific commands at a location that is not at given device.

Yet another aspect of the present teachings relates to a method of controlling the operation of a biological laboratory. The method comprises associating a translation component with an existing instrument such that the translation component translates transmitted state signals and received instructions based at least in part on the state signals so that the instrument can be instructed to facilitate capture of identification information about a biological sample being assayed. The method further comprises maintaining a directory of information for each of the translation components such that a user interface can determine by accessing the directory which instruments are available for use to determine an assay process based at least in part on the state signals and the resulting instructions. the method further comprises updating the directory whenever an instrument is either added or removed functionally from the biological laboratory such that the user interface can adjust the manner in which the state signals and instructions are implemented in the assay process based on the availability of the instruments in the biological laboratory.

In certain embodiments, associating the translation component with the instrument comprises configuring a front end component of the instrument to perform the translation of the states and the instructions. In other embodiments, associating the translation component with the instrument comprises configuring an algorithm not on the instrument to perform the translation of the states and the instructions.

In certain embodiments, maintaining the directory comprises a listing of instruments available for use. The list of instruments comprises information about the instruments such as supported interface types, physical locations of the instruments, and identifiers that allow communication via a network. Updating the directory comprises updating the list of instruments.

Yet another aspect of the present teachings relates to a system for controlling the operation of a biological laboratory having a plurality of biological processing devices. The system comprises a control system that monitors and controls the operation of the plurality of biological processing devices. The control system includes a standardized state logic having a plurality of standardized commands and a database that correlates a change of state of a biological processing device to a corresponding command among the plurality of standardized commands. The system further comprises a plurality of translation components associated with the plurality of biological processing devices. The plurality of translation components includes a customized instruction set that instructs the biological processing device to change from a first state to a second state in response to receiving the standardized state change command from the control system. The plurality of translation components include at least one sample analyzer translation component for at least one sample analyzer. The at least one sample analyzer translation component receives standardized commands from the control system such that the at least one sample analyzer is instructed by the at least one sample analyzer translation component to obtain identification information about the biological sample.

These and other aspects of the present teachings will become more apparent from the following description taken in conjunction with the accompanying drawings.

BRIEF DESCRIPTION OF THE DRAWINGS

FIGS. 2-1 to 2-5 illustrate how various devices can be integrated so as to be recognized by the control system.

FIG. 3 illustrates an exemplary standardized state diagram by which the control system operates to control the plurality of analytical devices.

FIG. 4 illustrates one possible process that the control system can use to routinely monitor the states of the devices in a standardized format and issue standardized commands in response to those states.

FIG. 5 illustrates one possible process that the control system can use to issue the standardized commands in response to the various standardized states.

FIG. 6 illustrates one possible implementation of the exemplary standardized commands into device-specific commands.

FIG. 7B illustrates a translation process that translates a device-specific state into a corresponding standardized state.

FIG. 7C illustrates a translation process that translates a standardized command into a corresponding device-specific command.

FIG. 9B illustrates an exemplary translation for a sample storage device of FIGS. 8A and B.

DETAILED DESCRIPTION OF CERTAIN EMBODIMENTS

Figure 1:
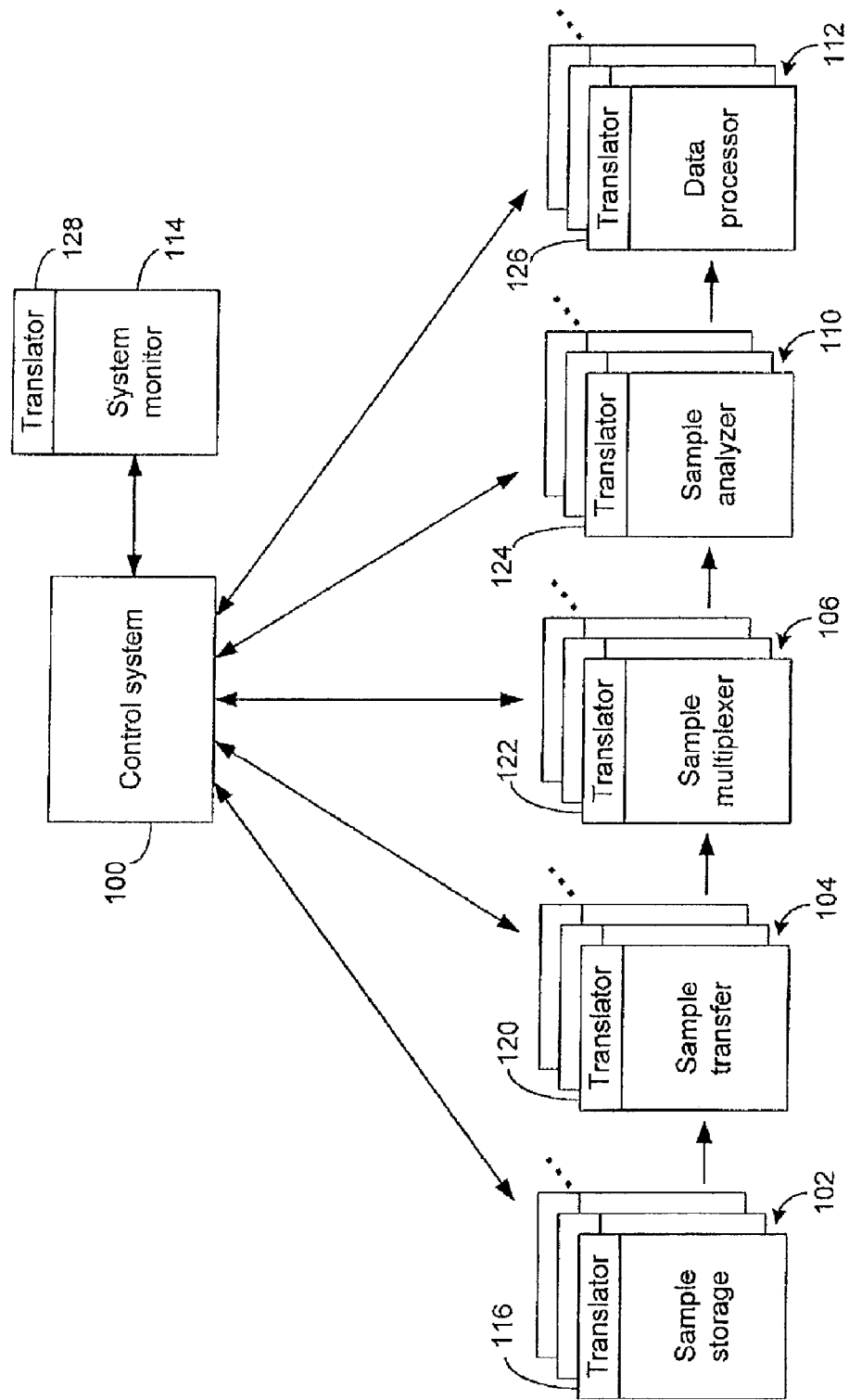
FIG. 1 illustrates a plurality of analytical devices being controlled by a control system via a translator.

These and other aspects, advantages, and novel features of the present teachings will become apparent upon reading the following detailed description and upon reference to the accompanying drawings. In the drawings, similar elements have similar reference numerals.

One aspect of the present teachings relates to a control system that communicates with a plurality of devices and facilitates coordinated functioning of the devices based on the states of the devices. FIG. 1 illustrates a functional block diagram showing a biological measurement related analytical system having a control system 100 in communication with some possible types of devices associated with biological measurements. Such devices may include, by way example, one or more sample storage device 102, one or more sample transfer device 104, one or more sample multiplexing device 106, one or more sample analyzing device 110, and one or more data processing device 112. The control system 100 may also be in communication with one or more system monitoring device 114. More specific examples of these devices are described below in the form of an exemplary sample analysis process.

It will be appreciated that any type of device not illustrated in FIG. 1 may be included in the analytical system without departing from the spirit of the present teachings. Moreover, the presence of the type(s) of device as illustrated in FIG. 1 does not necessarily mean that such a device is required in the analytical system.

In one aspect, the control system 100 comprises a state monitoring system that performs a standardized state monitoring procedure for the devices it communicates with. It will be appreciated that by standardizing the state configuration of the devices, the control system 100 can manage a relatively large number of devices in a simple manner.

As shown in FIG. 1, associate with each device is a translator that translates the communication between the control system 100 and the corresponding device. Translators 116, 120, 122, 124, 126, and 128 correspond to the devices 102, 104, 106, 110, 112, and 114, respectively. In one aspect, the translator translates device-specific state signals from the device into standardized state signals. The translator also translates a generally reverse process wherein the standardized command signals, in response to the standardized state signals, are translated into device-specific command signals. Thus, one can see that the translators allow the control system 100 to operate in a standardized mode, thereby allowing effective management of relatively large numbers of different types of devices.

In FIG. 1, the translators are depicted as being adjacent the devices It will be appreciated, however, that the translator may reside in any number of locations including, but not limited to, the front end component of the device, the control system, or some form of a repository accessible by the control system. It will also be appreciated that the translator (and the control system) may be implemented in various forms of a processor.

In general, it will be appreciated that the processors comprise, by way of example, computers, program logic, or other substrate configurations representing data and instructions, which operate as described herein. In other embodiments, the processors can comprise controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

FIGS. 2-1 to 2-5 illustrate a manner in which various devices can be integrated into a laboratory system. Such an advantageous manner is described in greater detail in a copending application titled "System and Method for Open Control and Monitoring of Biological Instruments," Ser. No. 10/455,262, which is hereby incorporated by reference in its entirety.

For the purpose of describing a possible architecture that could facilitate the present teachings of this application, FIGS. 2-1 to 2-5 are duplicates of FIGS. 1 to 5 of the Ser. No. 10/455,262 application. To avoid confusion, a "2-" prefix has been added to each of the reference numerals for numbered elements in FIGS. 2-1 to 2-5.

Figures 1, 2:
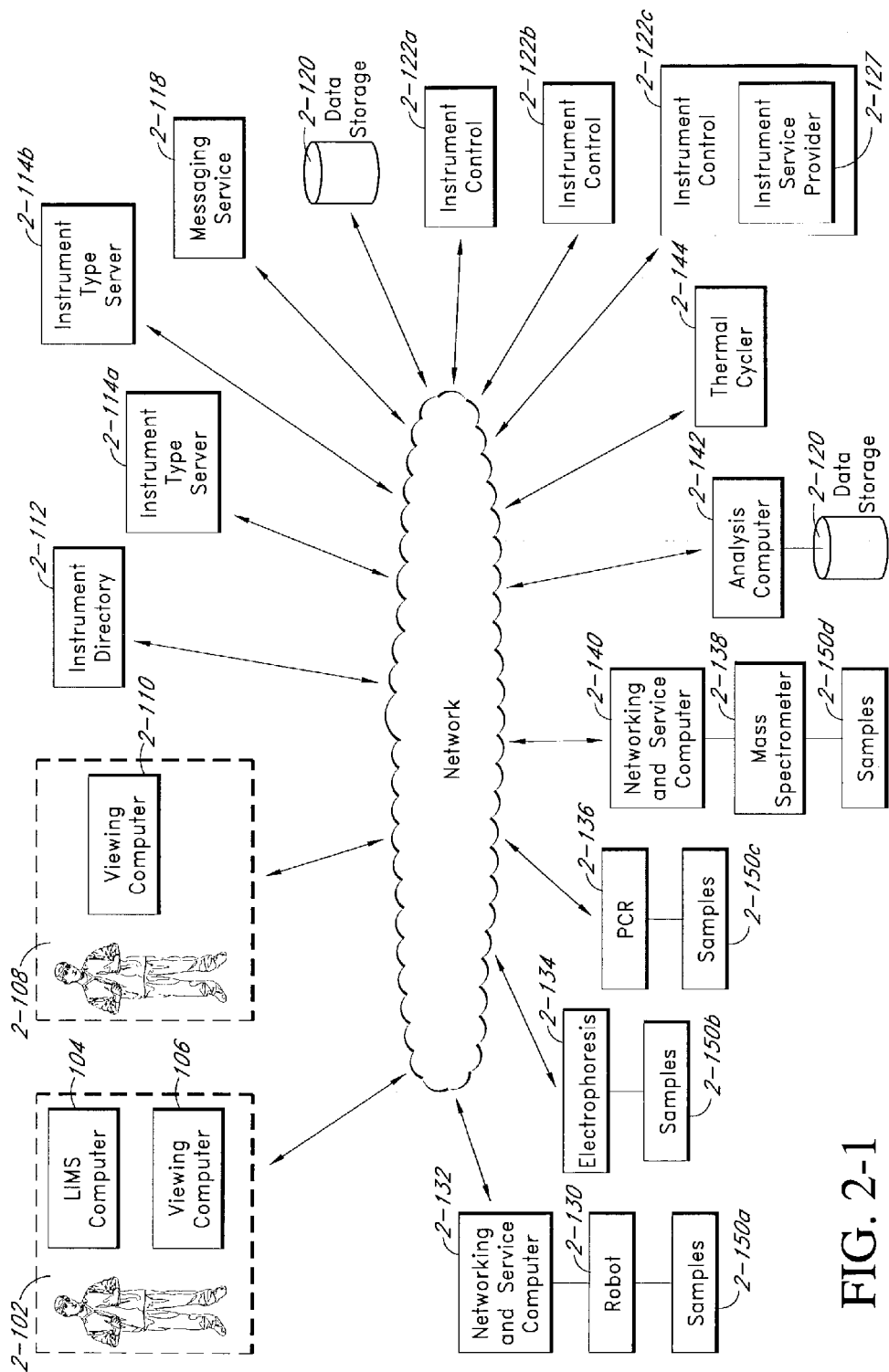
Figure 2:
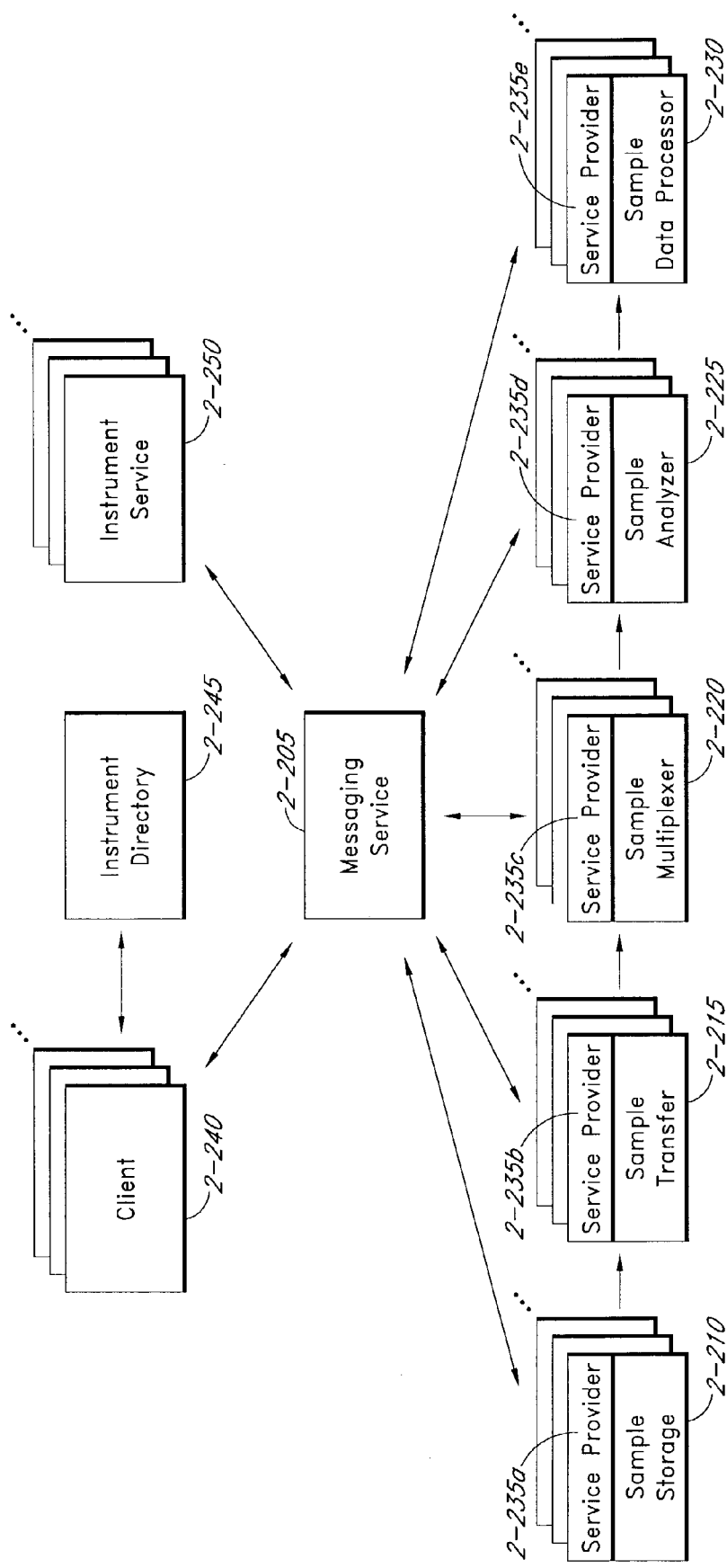

FIG. 2-1 illustrates an integration framework of a biological laboratory system having a plurality of exemplary devices indicated as a robot 2-130, an electrophoresis device 2-134, a PCR 2-136, a mass spectrometer 2-138, an analysis computer 2-142, and a thermalcycler 2-144. Such devices may be connected to a common network, and be managed by a management system 2-104 via the common network. The management of the devices may be facilitated by an instrument directory 2-112 that includes information about the devices. Such information may include the types of interfaces supported by the devices, device-specific information such as serial number and physical location, and identifiers that allow communication via the network. In certain embodiments, the instrument directory 2-112 also includes a list of updated devices that are available for use.

The management of the devices may also be facilitated by an instrument-type service provider 2-114. In certain embodiments, the instrument-type service provider 2-114 provides the management system 2-104 with information about various devices' requirements so that the management system 2-104 can monitor and control the devices in an appropriate manner.

The management of the devices may also be facilitated by a messaging service 2-118. The messaging service 2-118 allows communication between the various management-related entities (e.g., management system, instrument directory, instrument-type service provider, and other entities described below), various devices, and other entities in the laboratory system. In certain embodiments, the messaging service 2-118 provides such communication without having to rely on a direct communication between components.

The management of the devices may also be facilitated by an instrument control component 2-122. In certain embodiments, the instrument control component 2-122 comprises a computing device configured to run a service provider software 2-123. Such software may be configured to provide control over the devices as well as provide devices' status updates to the management system 2-104. In certain embodiments, the service provider software 2-123 may implement one or more software interfaces that allow communication between the management-related components with the various devices in a meaningful manner.

The management of certain devices in the laboratory system may also be facilitated by networking/service computers (indicated as 2-132 and 2-140 in FIG. 2-1). Such computers may provide improved communication with devices that do not have their own networking and communication capabilities. Thus, the networking/service computers emulate the desired networking and communication functionality for their respective devices.

FIG. 2-2 illustrates one possible routing of communication between a client 2-235 and a plurality of exemplary devices (2-210, 2-215, 2-220, 2-225, and 2-230). The client 2-235 entity may include the management system described above in reference to FIG. 2-1. In the exemplary communication scheme of FIG. 2-2, an instrument directory 2-240 provides the client 2-235 with information about the devices. Then, the communication between the client 2-235 and the device(s) is facilitated via a messaging service 2-205. The messaging service 2-205 may rely on an instrument-type service provider 2-245 to format the communication according to the devices' requirements.

FIGS. 2-3A and 2-3B illustrate two possible modes of communication between the various components. In a point-to-point method, a communication between a client and a device is performed in a generally chained manner. In an exemplary chain, a message from the client goes through a messaging service, through an instrument software, and then to the destination device (instrument hardware in FIG. 2-3A).

Figures 2, 3, 3A:
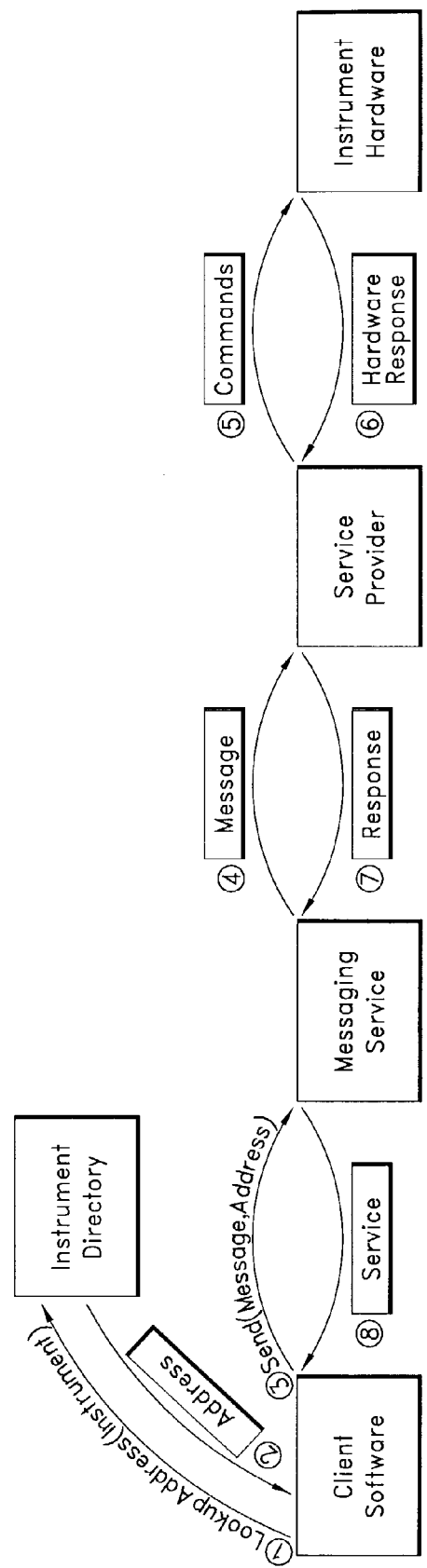
Figures 2, 3, 3B:
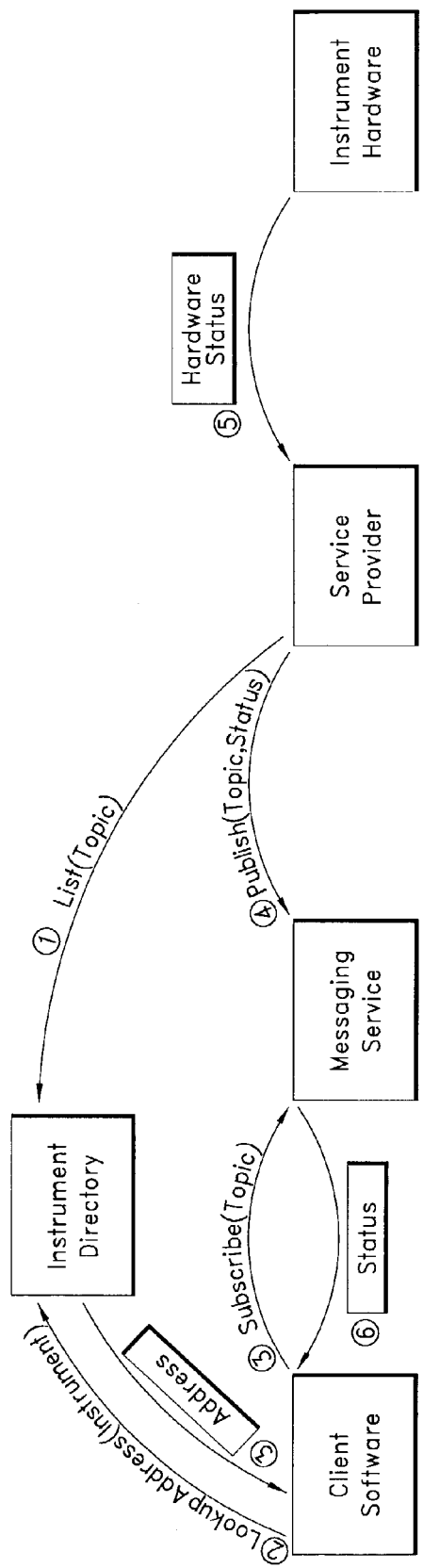

FIG. 2-3B illustrates a publish/subscribe messaging method. In an exemplary communication where the device wants to send a message to the client, the device sends a status signal to the instrument software that in response publishes that status (along with an appropriate topic) to the messaging service. The messaging service does not automatically relay the status message to the client. Instead, the client subscribes to the messaging service with an appropriate topic. The messaging service matches the topic from the instrument software with that from the client, and sends the corresponding status message to the client.

Figures 2, 3, 4:
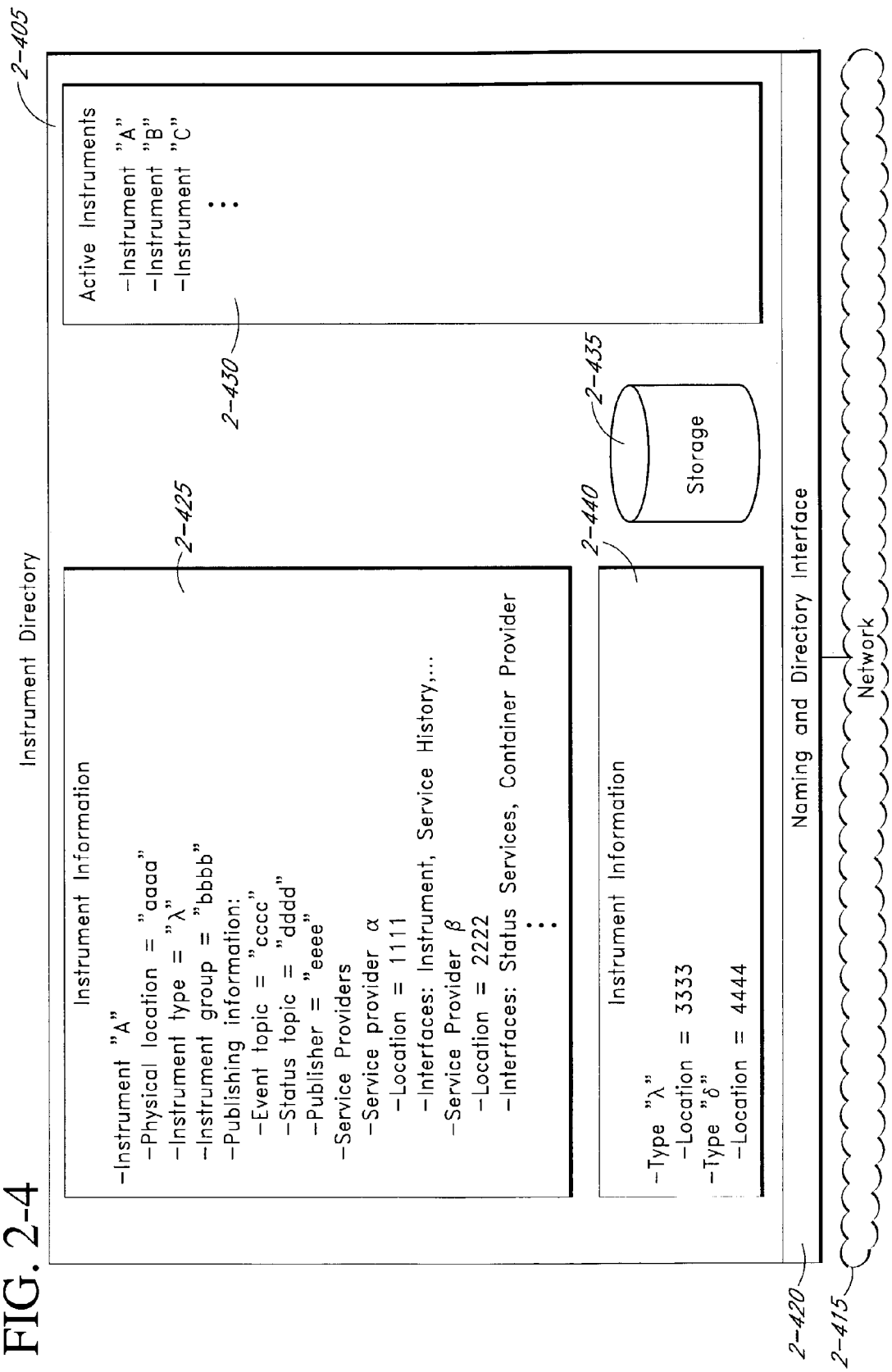

FIG. 2-4 illustrates an exemplary instrument directory 2-405. Such a directory may include an instrument information 2-425 that contains information such as instrument name, physical location, type, group, publishing information, and other information useful for management of the instrument (device). The directory 2-405 may also include an instrument type provider information 2-440 that contains information about the instrument-type service provider described above in reference to FIGS. 2-1 and 2-2. The directory 2-405 may also include a list 2-430 of active instruments. The directory 2-405 may also include a storage device for storing information that facilitates various functions of the directory. The directory 2-405 is also shown to be connected to a network 2-415 so as to allow communication with other components.

Figures 2, 3, 4, 5:
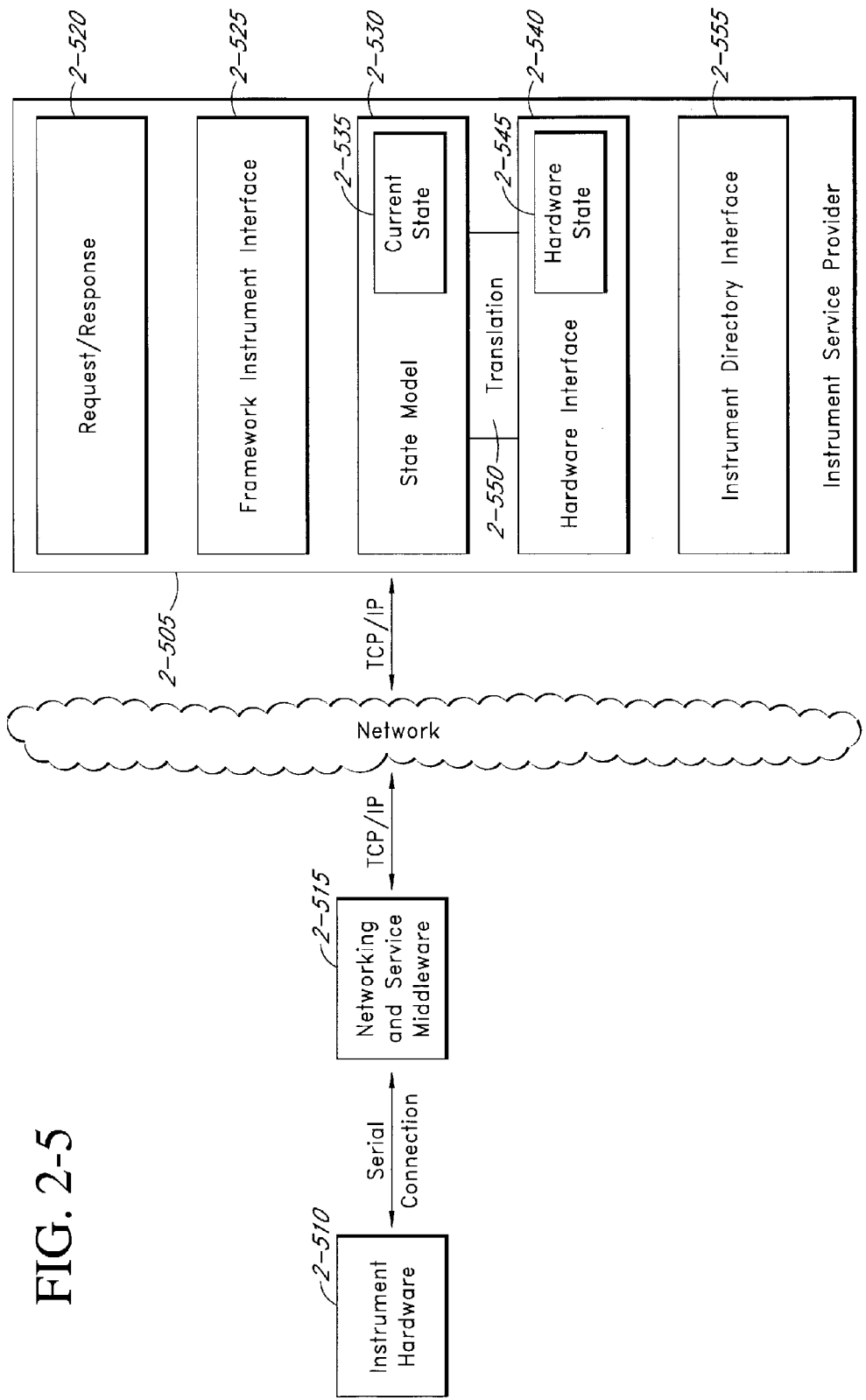
Figure 3:
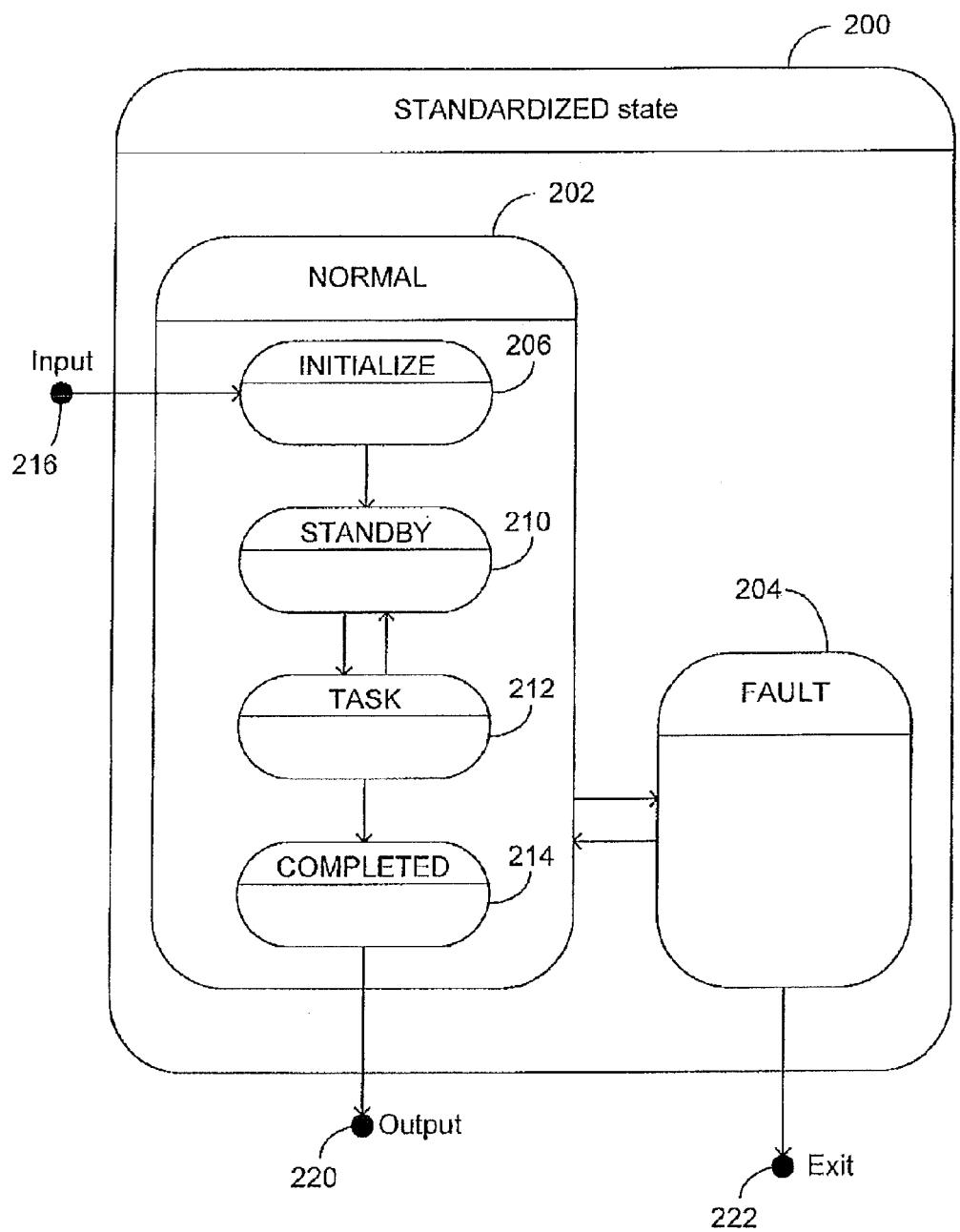
Figure 4:
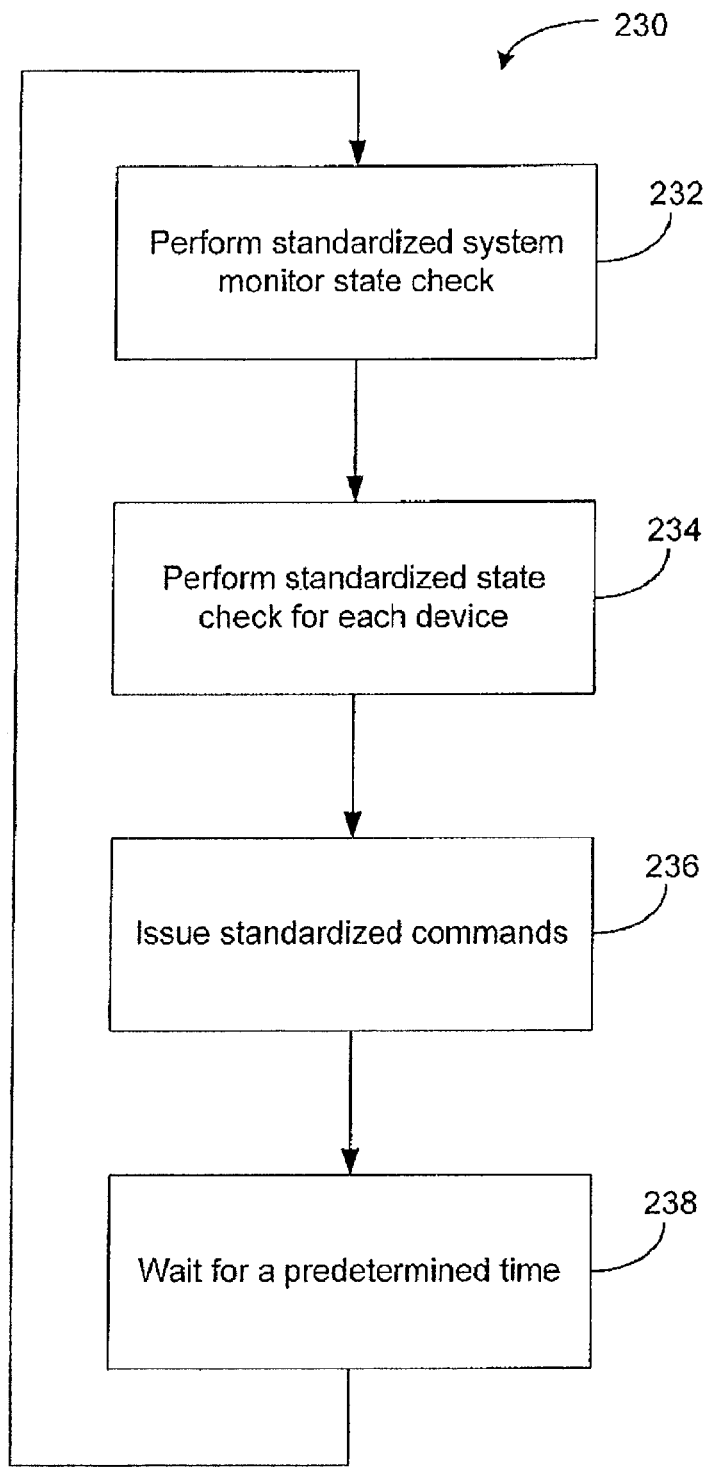
Figure 5:
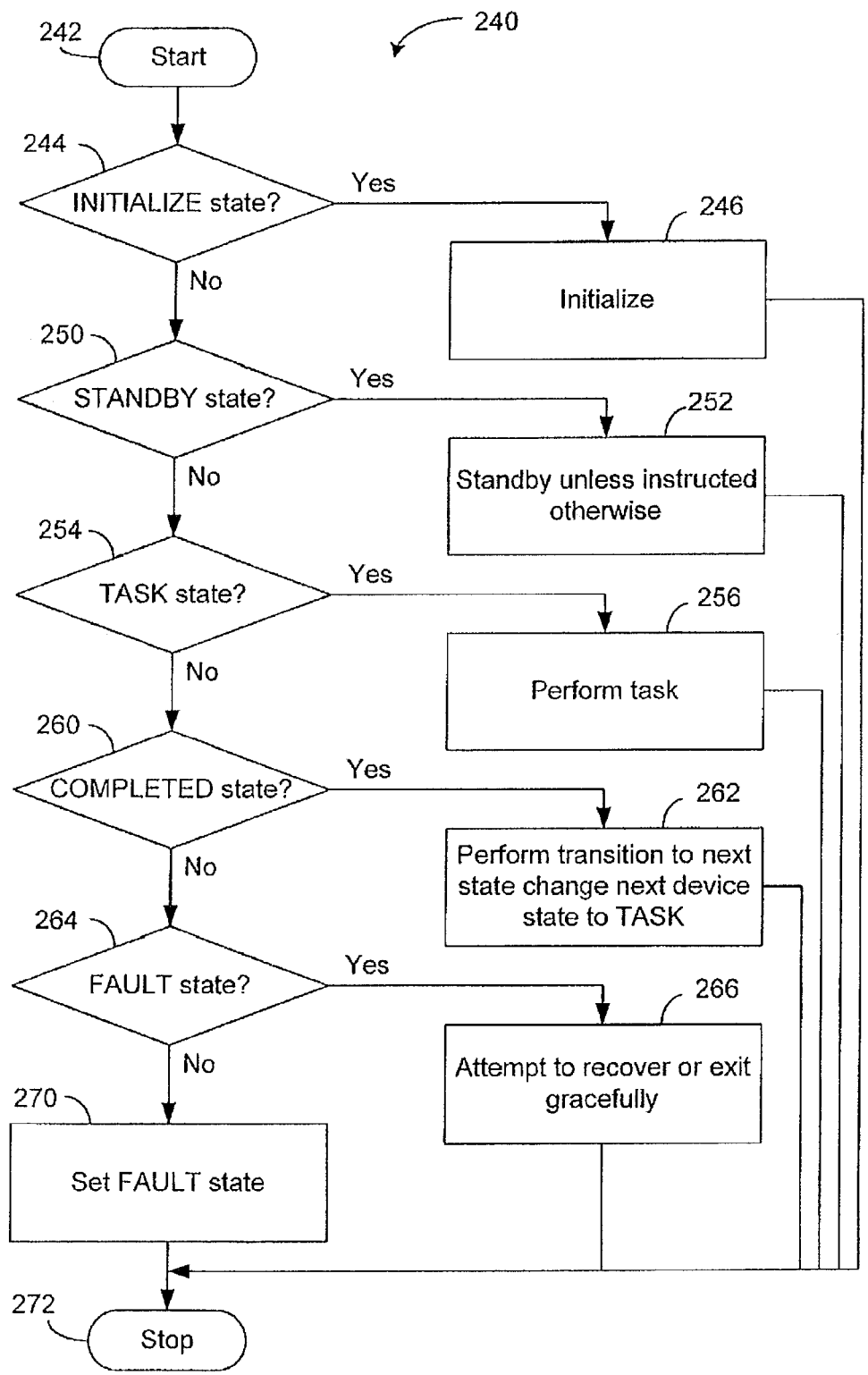

FIG. 2-5 illustrates a possible functional relationship between an instrument hardware 2-510 and an instrument service provider 2-505 (described above in reference to FIG. 2-1). The hardware is depicted to be in communication with a networking and service middleware 2-515. Such middleware may be an integral part of the instrument, or may be an emulating component (networking and service computer in FIG. 2-1). The middleware 2-515 is in communication with other networked components via a network 2-508. The instrument service provider 2-505, also networked with the middleware 2-515, may include a plurality of functionalities, including a state model component 2-530 and a hardware commands component 2-540. Various aspects of the state model component and the hardware command component are described below in greater detail.

From the brief description of the integration framework in reference to FIGS. 2-1 to 2-5, it will be appreciated that the present teachings may be implemented in such a framework in a number of ways. For example, entities described herein as "translators" may be incorporated as part of the instrument service provider (FIG. 2-5). Similarly, entities described herein as "translations" may be part of the instrument interface (FIG. 2-4). It should be understood, however, that the various aspects of the present teachings may be implemented in systems other than that of the aforementioned framework without departing from the spirit of the present teachings.

FIG. 3 now illustrates one possible configuration of a standardized state 200 having an external input 216, and external output 220, and an external exit 222. The standardized state 200 is depicted to be categorized into a NORMAL state 202 and a FAULT state 204. Within the NORMAL state 202 are INITIALIZE state 206, STANDBY state 210, TASK state 212, and COMPLETED state 214. Throughout the description, the standardized states at the control system level are indicated by capital letters, and the device-specific states at the device level are indicated by lowercase letters. It should be understood that such convention is for the descriptive purpose, and in no way meant to limit the scope of the present teachings.

The standardized configuration of the standardized state 200 may represent any one of the devices in communication with the control system 100. Given such a set of standardized states, it is possible to construct and implement a standardized process for controlling the devices without worrying about device-specific parameters. Such device-specific parameters may include various states of the device as well as commands, understandable by the device, that change the device's states. It should be apparent that having such a standardized process facilitates easier arranging of functional relationships of the various devices.

It will be appreciated that the content of the standardized state 200 described in reference to FIG. 3 is exemplary, and is not intended to limit the scope of the present teachings. Various applications of systems of biological measurement devices may lead to such standardized state being configured in different manners. The concept of utilizing such a standardized state to effectively monitor and control a plurality of devices, however, is one aspect of the present teachings.

FIG. 4 illustrates one possible process 230 that utilizes the standardized state 200. The process 230 may be initiated (not shown) in the control system 100, and the process 230 may run in a continuous or periodic manner during the sample analysis process. Although the process 230 is depicted as a loop, it will be appreciated that such repetitive process execution may be implemented in any number of ways known in the art without departing from the spirit of the present teachings.

In FIG. 4, the looping process 230 comprises step 232 where the process 230 performs a standardized system monitor state check. In step 234 that follows, the process 230 performs a standardized state check for the devices recognized by the control system 100. It will be appreciated that in certain implementations, the system monitor device (114 in FIG. 1) may be treated as one of the analysis-related devices. The standardized state and command system and method described herein treats global devices (such as the system monitor device) as a compatible devices. Thus, it will be appreciated that steps 232 and 234 may be combined as a single step without departing from the spirit of the present teachings.

Following step 234, the process 230 issues standardized state commands in step 236 based on the monitored states. In step 238 that follows, the process 230 waits for a predetermined time before looping back to step 232. The predetermined time may be selected to be any value.

FIG. 5 illustrates a process 240 that may occur during a portion of a single cycle of the process 230 of FIG. 4. In particular, the process 240 depicts one possible way the control system can issue standardized commands to a given device in response to the standardized states monitored. Thus, the process 240 may occur during step 236 of the process 230 described above in reference to FIG. 4.

The process 240 begins at a start step 242, and proceeds through a series of checks for the exemplary standardized states previously described in reference to FIG. 3. The process 240 in decision step 244 determines if the device is in INITIALIZE state. If yes, then the process 240 in step 246 issues a command instructing the device to initialize. If no, then the process 240 proceeds to act on the next standardized state for the device.

The process 240 in decision step 250 determines if the device is in STANDBY state. If yes, then the process 240 in step 252 issues a command instructing the device to remain in the standby mode. If no, then the process 240 proceeds to act on the next standardized state for the device.

The process 240 in decision step 254 determines if the device is in TASK state. If yes, then the process 240 in step 256 issues a command instructing the device to perform its assigned task. If no, then the process 240 proceeds to act on the next standardized state for the device.

The process 240 in decision step 260 determines if the device is in COMPLETED state. If yes, then the process 240 in step 262 issues a command instructing the next device (that functionally follows the COMPLETED device) to perform its task if able to. Thus, the process 240 changes the standardized state of the next device to TASK. If the answer in the decision step 260 is no, then the process 240 proceeds to act on the next standardized state for the device.

The process 240 in decision step 264 determines if the device is in FAULT state. If yes, then the process 240 in step 266 issues a command instructing the device to attempt recovery or exit gracefully. If no, then the process 240 in step 270 sets the device's standardized state to FAULT since its state was indeterminate. The process 240 ends at step 272.

The process 240 is an exemplary process that shows how the control system may issue standardized commands to devices based on the standardized states obtained from the same devices. It will be appreciated that such a process can be implemented in any number different ways utilizing different programming logic and algorithm.

The exemplary process 240 of FIG. 5 is performed for each of the devices in communication with the control system. FIG. 6 now illustrates a summary table 274 of the commands (in response to the standardized states) for the devices described above in reference to FIG. 1. It should be realized that the commands listed in table 274 are exemplary for the purpose of describing a concept of how the control system can issue standardized commands to coordinate the sequence of different tasks performed by the devices.

The exemplary commands in response to INITIALIZE state are selected to be generally similar—initialize the device if not already initialized. The exemplary commands in response to STANDBY state are also selected to be similar—continue to standby. The exemplary commands in response to TASK state are also selected to be similar—continue the device's assigned task. It will be understood that different types of devices will likely have different means for initializing, standing by, and performing their respective tasks.

The exemplary commands in response to COMPLETED state allows transition of the sample between the devices in the analytical system. For the devices illustrated in FIG. 1, the sample analysis process progresses sequentially from the sample storage (102) to the data processor 112. Thus, if the sample storage is COMPLETED, the control system changes the next device (sample transfer) to TASK if in STANDBY state. Similarly, sample transfer device COMPLETED causes the control system to change the multiplexer to TASK if in STANDBY state. Similarly, multiplexer COMPLETED causes the control system to change the sample analyzer to TASK if in STANDBY state. Similarly, sample analyzer COMPLETED causes the control system to change the data processor to TASK if in STANDBY state. If the data processor is the last device in the analytical sequence, its COMPLETED state may cause the control system to end the analysis process. For the system monitor device, the COMPLETED state may not be applicable since the device may be configured to monitor the analytical system during and possibly beyond the analysis process.

For the analytical devices, the exemplary commands in response to FAULT state are selected to be generally similar—attempt to recover or exit gracefully. Different devices may have different recovery and exit processes. For the system monitor device, the exemplary command in response to FAULT comprises a "system halt" to shut down the system. Some system monitoring devices and conditions that may give rise to such a command are described below.

Figure 7A:
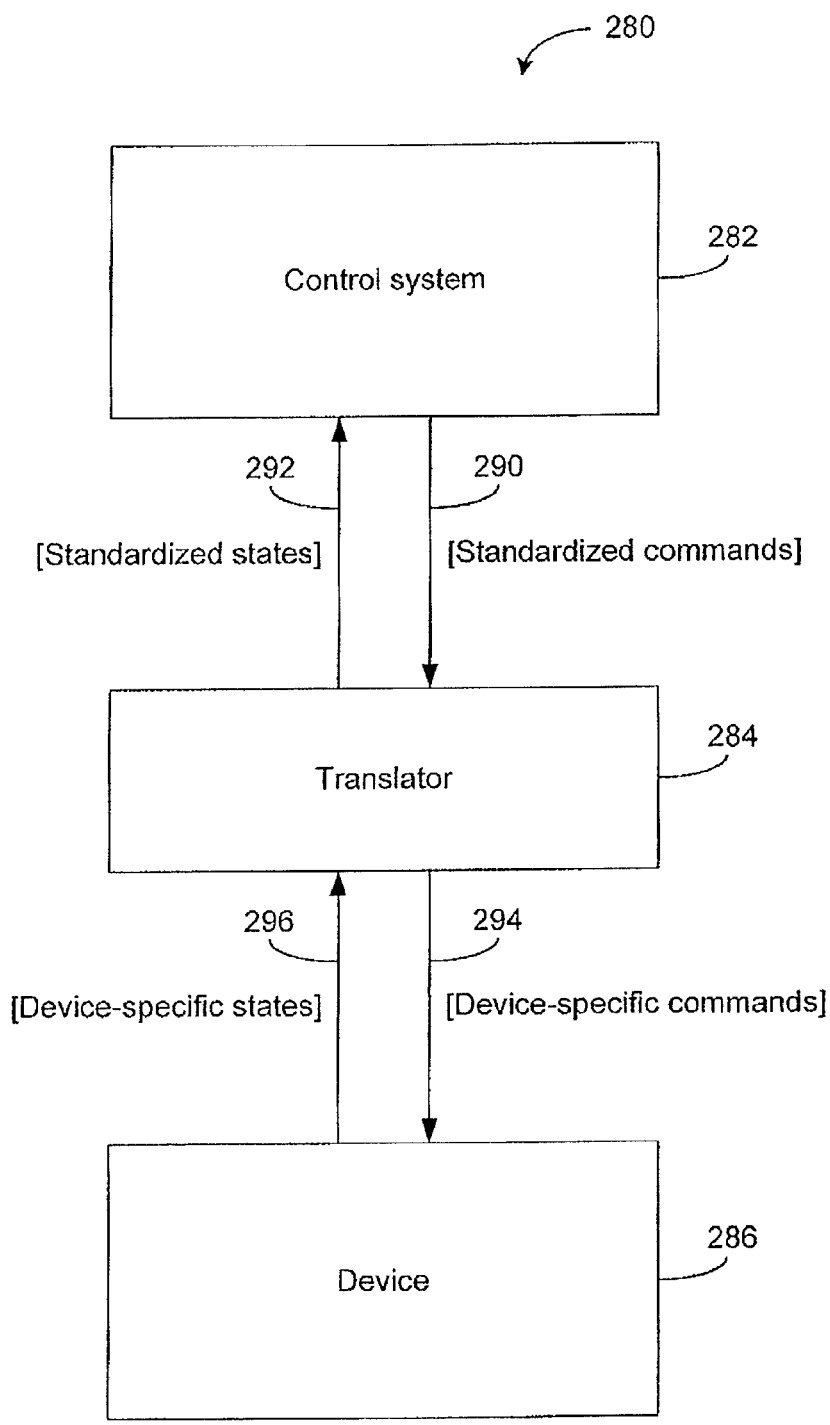
FIG. 7A illustrates a translator that translates the device-specific states into standardized states and the standardized commands into device-specific commands.

As previously described, the control system monitors and coordinates the plurality of devices based on standardized states and commands via the translator. FIG. 7A now illustrates a functional block diagram 280 that shows one possible way of implementing such a functionality. A translator 284 is functionally interposed between a control system 282 and a device 286. The translator 284 interacts with the control system 282 in standardized state (arrow 292) and command (arrow 290) formats. The translator 284 also interacts with the device 286 in device-specific state (arrow 296) and command (294) formats. As previously described such a translator may functionally reside in the device, control system, or anywhere that allows such translation between the control system and devices. One possible manner in which the translation can be implemented is described below by way of example.

FIGS. 7B-C now illustrate possible processes that may be implemented to carry out the function of the translator described above in reference to FIG. 7A. FIG. 7B illustrates a device-to-controller translation process 600 that begins at a start step 602. In step 604 that follows, the process 600 receives from the device a signal representative of a state of the device. In step 606 that follows, the process 600 determines a STANDARDIZED STATE corresponding to the device state. Such determination may be achieved by providing the translator with a predetermined assignment scheme that assigns the device's various states to their corresponding STANDARDIZED STATES. In step 610 that follows, the process 600 transmits the STANDARDIZED STATE to the controller. The process 600 ends at a stop step 612.

FIG. 7C illustrates a controller-to device translation process 620 that begins at a start step 622. In step 624 that follows, the process 620 receives from the controller a signal representative of a STANDARDIZED COMMAND intended for the device. In step 626 that follows, the process 620 determines a device-specific command corresponding to the STANDARDIZED COMMAND. Such determination may be achieved by providing the translator with a predetermined assignment scheme that assigns the controller's various STANDARDIZED COMMANDS to their corresponding device-specific commands. In step 630 that follows, the process 620 transmits the device-specific command to the device. The process 620 ends at a stop step 632.

FIGS. 8-9 illustrate an exemplary analysis process in terms of states and state-based commands facilitated by an exemplary translation. An exemplary analysis system 300 comprises analysis related devices sample storage unit 304, robotics 306, thermalcycler 310, mass spectrometer 312, sequencer 314, electrophoresis unit 316, array unit 320, and data processor 322. The analysis system 300 further comprises a system monitor device 302. The aforementioned devices are functionally connected to a control system 308 through their corresponding translators (326, 330, 332, 334, 336, 340, 342, 344, and 324, respectively).

It will be appreciated that the exemplary system 300 may be a standalone system or a part of a larger system having a plurality of such exemplary systems. Such a larger system may operate the plurality of the exemplary systems independently from each other. In such operating configuration, the system monitor may monitor the operating condition(s) associated with more than one exemplary system. The larger system may also be configured such that components of the different exemplary systems can be "mix-and-matched" as needed. It will be appreciated that such flexibility in reconfiguring of components is facilitated by the standardized format of the states and commands that are processed by a control system.

Figure 8A:
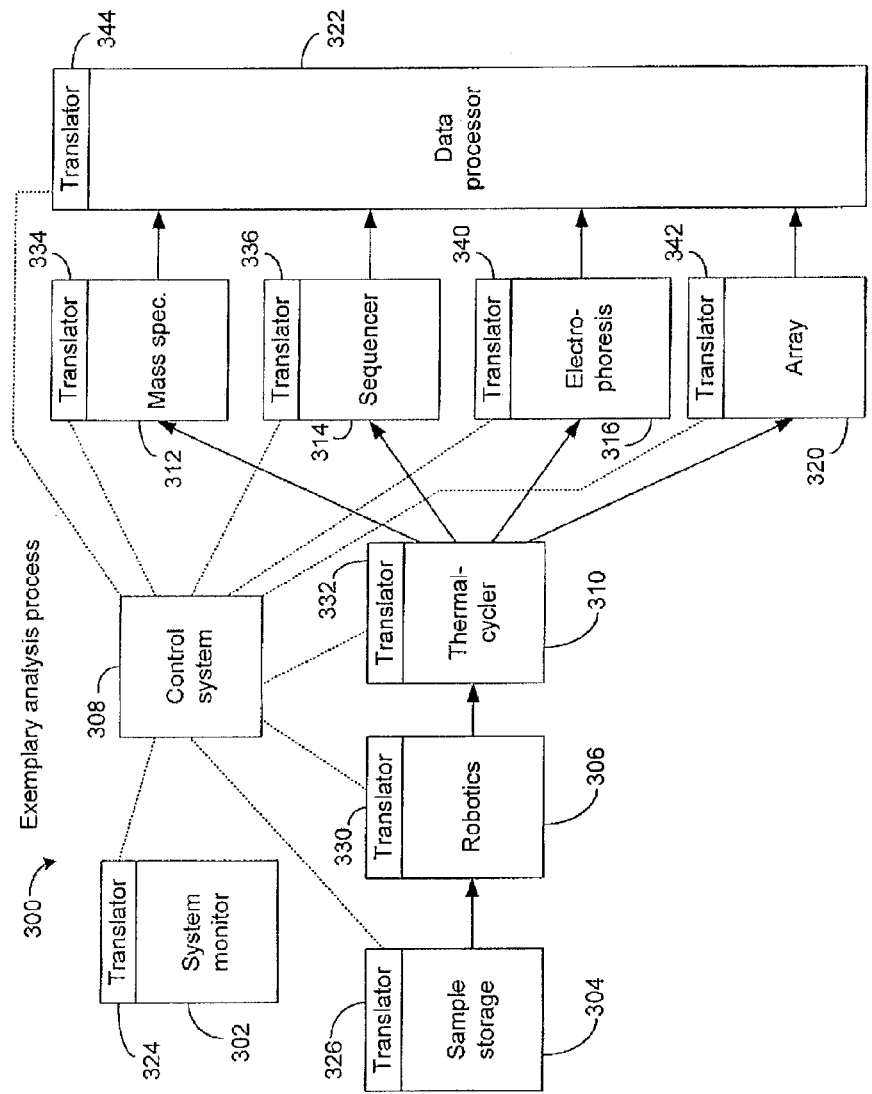
FIG. 8A illustrates an exemplary system of analytical devices adapted to multiplex a DNA sample into a plurality of measurement devices, wherein each of the devices is controlled by a control system via a translator.

FIGS. 8B-8J now illustrate some of the possible exemplary states that the various devices of FIG. 8A can be in. The states are logically organized into groups that generally mirror the organization of the standardized state described above in reference to FIG. 3. It will be appreciated that some of the devices may be relatively complex and can have many possible states other than those illustrated for the purpose of the description herein. Thus, a state diagram for each device depicts just few states representative of parameters that could be associated with the device. It will be appreciated that such representation of the device and its states is not intended to limit the scope of the present teachings.

Figure 8B:
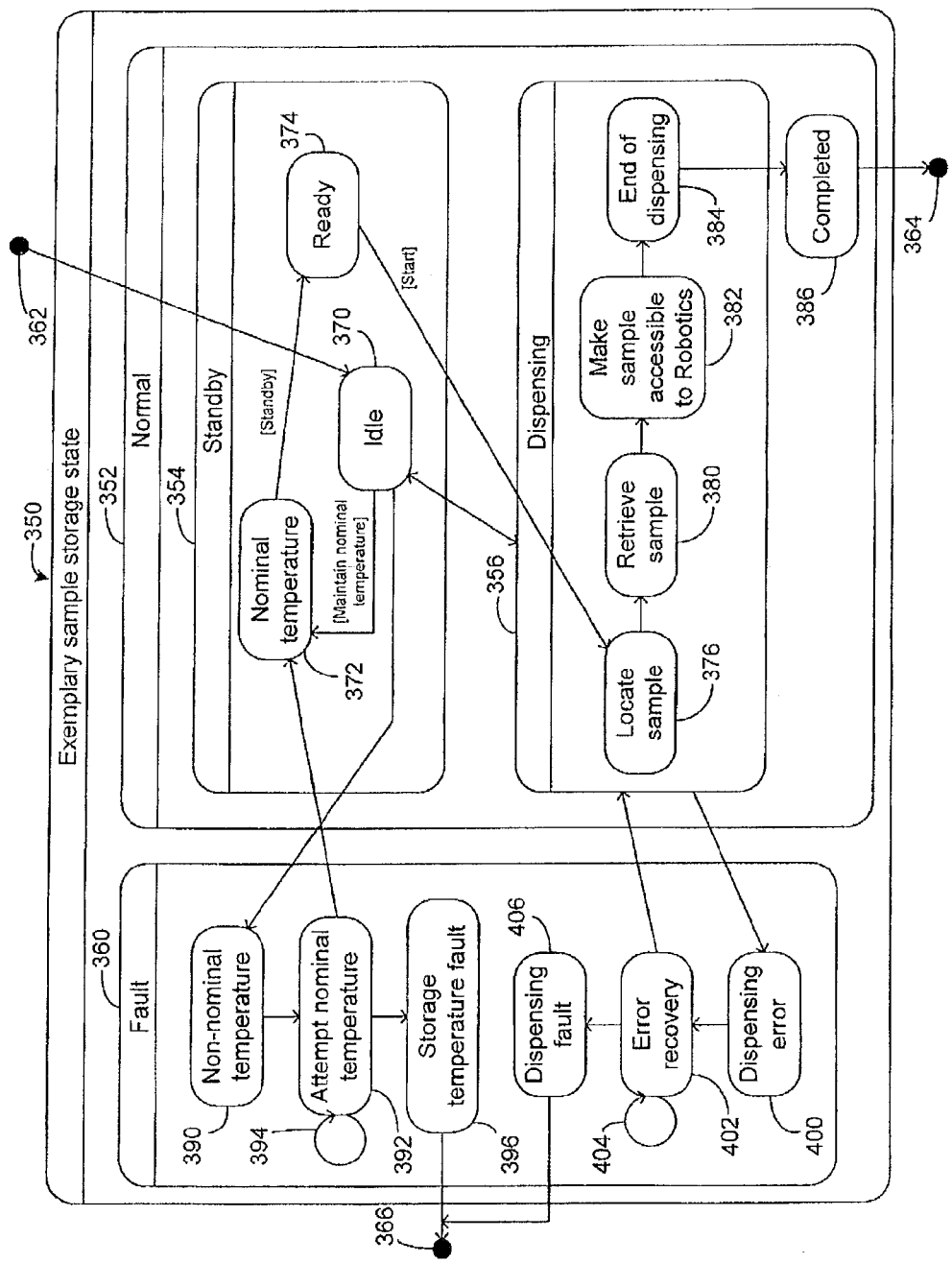
FIGS. 8B to 8J illustrate device-specific state diagrams showing various states associated with an exemplary feature of each device.

FIG. 8B illustrates an exemplary state 350 for the sample storage unit (304 in FIG. 8A). Some of the possible states within the storage unit is depicted to be grouped into a normal state 352 and a fault state 360. Within the normal state 352, states are further grouped into a standby state 354, a dispensing state 356, and a completed state 386.

A storage temperature parameter is selected, for the purpose of description, to represent possible states of the storage unit. Thus, the standby state 354 may include an "idle" state 370, a "nominal temperature" state 372, and a "ready" state 374. The dispensing state 356 may include a "locate sample" state 376, a "retrieve sample" state 380, a "make sample accessible to robotics" state 382, and an "end of dispensing" state 384. The fault state 360 may include a "non-nominal temperature" state 390, an "attempt nominal temperature" state 392, a "storage unit temperature fault" state 396, a "dispensing error" state 400, an "error recovery" state 404, and a "dispensing fault" state 406. The storage unit state 350 may also include an entry point 362, an normal exit point 364, and a fault exit point 366.

The storage unit may be configured such that in a typical normal operating sequence, the storage unit enters into the "idle" state 370 via the entry point 362. From the "idle" state 370, the unit transitions to the "nominal temperature" state 372 if the unit is able to maintain a nominal temperature. The unit then transitions to the "ready" state 374, and remains there until instructed to go into the dispensing state 356.

When the storage unit transitions from the standby state 354 to the dispensing state 356, the unit goes from the "ready" state 374 to the "locate sample" state 376. Subsequently, as the unit performs its dispensing function, it goes to the "retrieve sample" state 380, followed by the "make sample accessible to robotics" state 382 and the "end of dispensing" state 384. The unit then transitions from the dispensing state 356 to the completed state 386, and from there exits via the exit point 364.

During the standby and/or dispensing states 354 and 356, the unit may experience various types or malfunctions or errors. For example, during the "idle" 370 to "nominal temperature" 372. transition, if the unit is not able to maintain a nominal temperature, it may transition to the "non-nominal temperature" state 390 of the fault state 360 (instead of going to the "nominal temperature" state 372). Once in the fault state 360, the unit transitions to the "attempt nominal temperature" state 392, and while there, attempts to establish and maintain a nominal temperature (as indicated by a loop 394). If the attempt is successful, the unit transitions to the "nominal temperature" state 372 to resume the standby operation. If the attempt fails, the unit transitions to the "storage temperature fault" state 396. From there, the unit exits the operational mode via the exit point 366.

The unit may also experience an error during any states of the dispensing state 356. Such an error can cause the unit to transition from the dispensing state 356 to the "dispensing error" state 400 of the fault state 360. Once in the "dispensing error" state 400, the unit transitions to the "error recovery" state 402, and while there, attempts to recover from the error (as indicated by a loop 404). If the attempt is successful, the unit transitions back to the dispensing state 356 to resume the dispensing operation. If the attempt fails, the unit transitions to the "dispensing fault" state 406. From there, the unit exits the operational mode via the exit point 366.

Figure 8C:
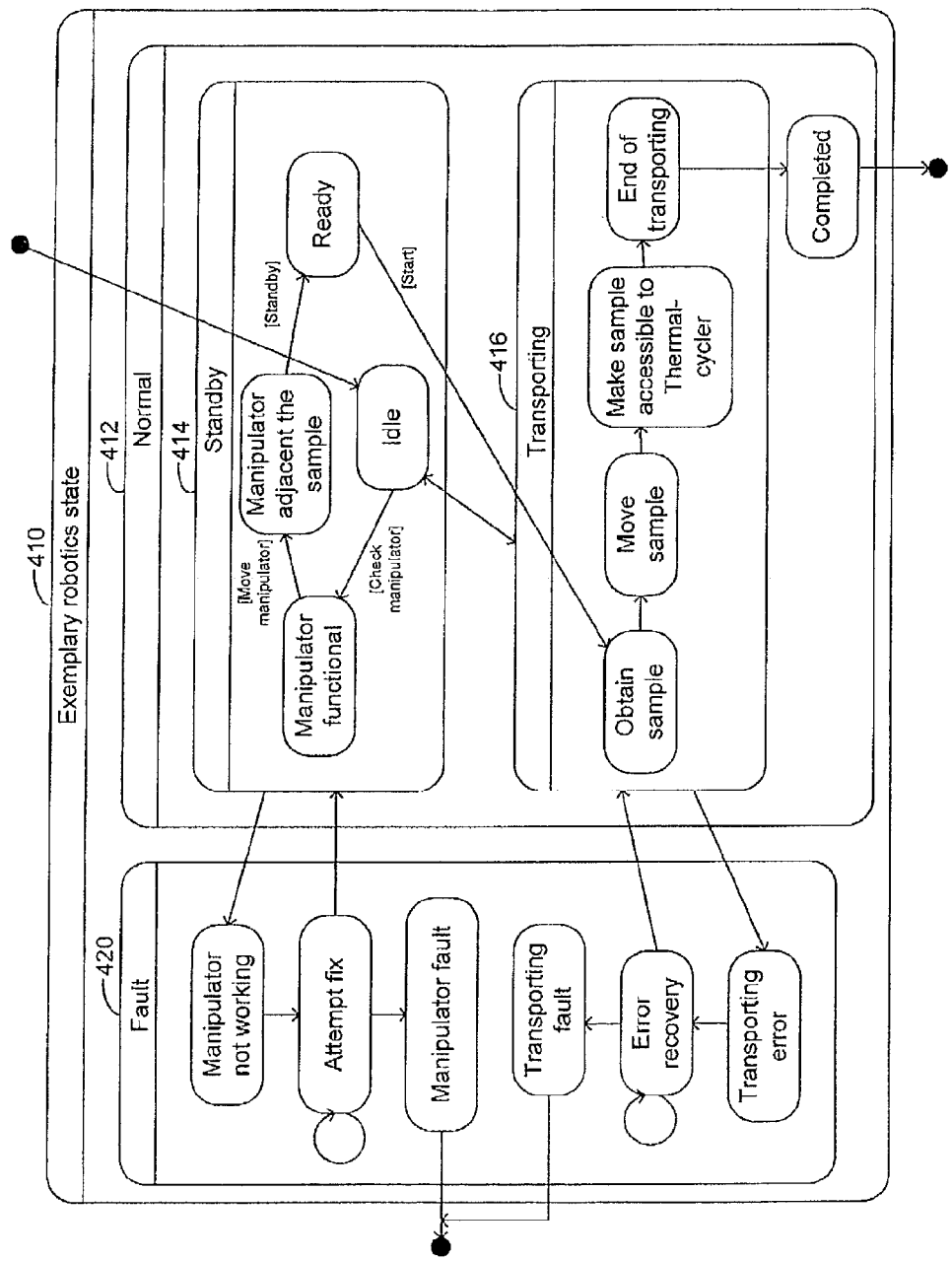

FIGS. 8C-J illustrate similar state transition diagrams for the other exemplary devices illustrated in FIG. 8A. FIG. 8C illustrates a state 410 of the robotics device. The device state 410 comprises a normal state 412 having a standby state 414 and a "transporting" state 416, and a fault state 420. For this device, a manipulator's function is selected to represent the various exemplary states in a manner similar to that described above in reference to FIG. 8B.

Figure 8D:
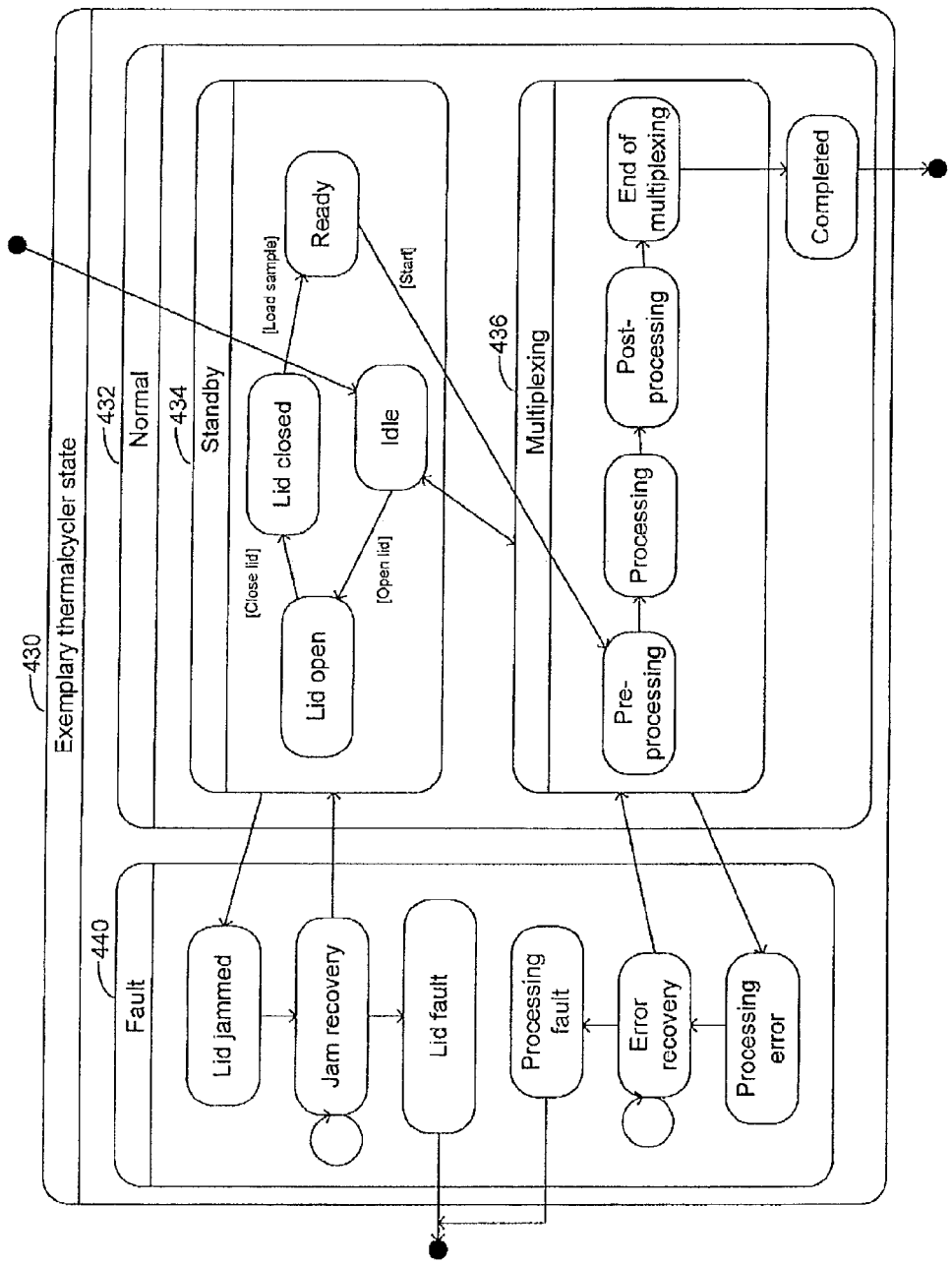

FIG. 8D illustrates a state 430 of the thermalcycler device. The device state 430 comprises a normal state 432 having a standby state 434 and a "multiplexing" state 436, and a fault state 440. For this device, a lid position of the device is selected to represent the various exemplary states in a manner similar to that described above in reference to FIG. 8B.

Figure 8E:
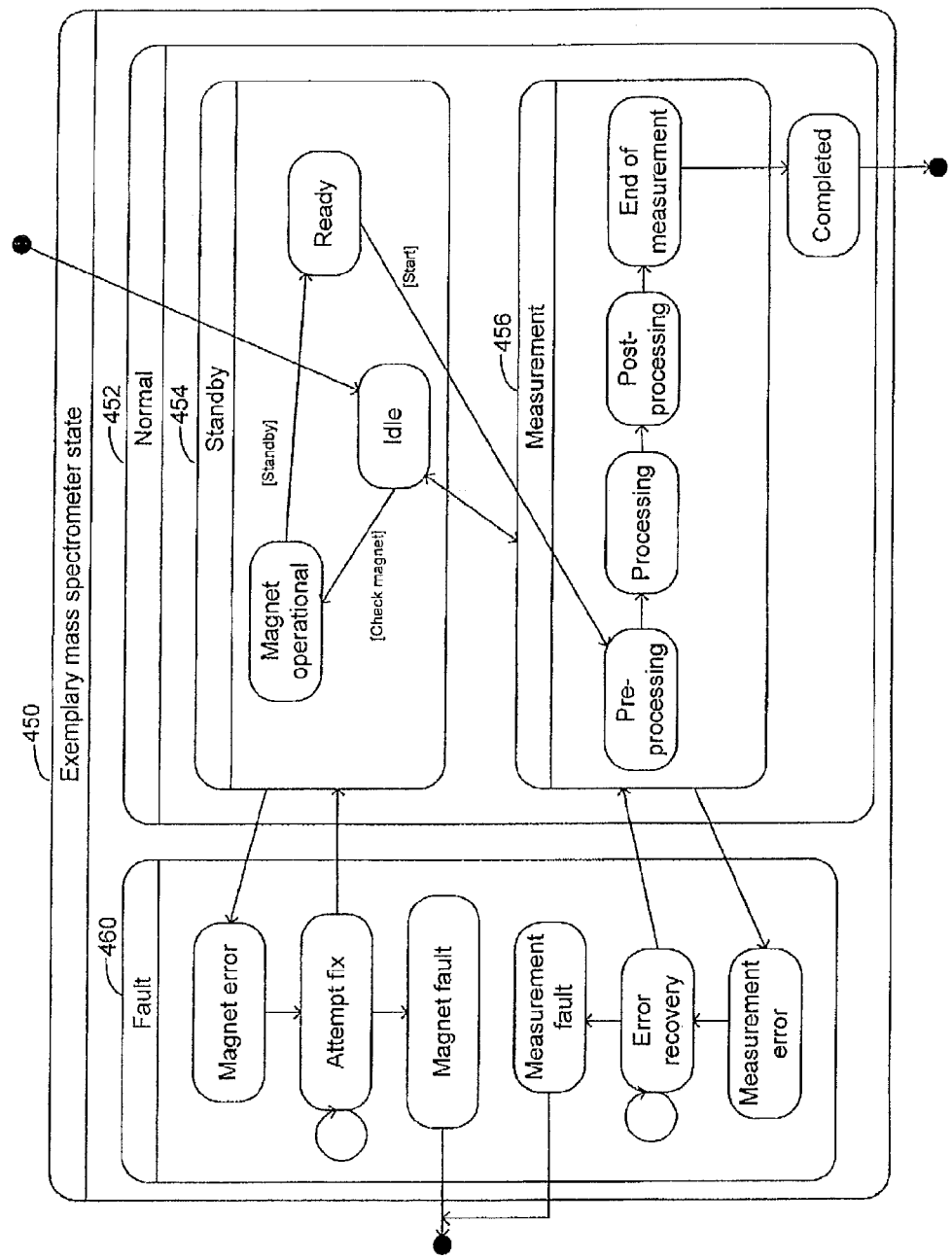

FIG. 8E illustrates a state 450 of the mass spectrometer device. The device state 450 comprises a normal state 452 having a standby state 454 and a "measurement" state 456, and a fault state 460. For this device, a magnet's function is selected to represent the various exemplary states in a manner similar to that described above in reference to FIG. 8B.

Figure 8F:
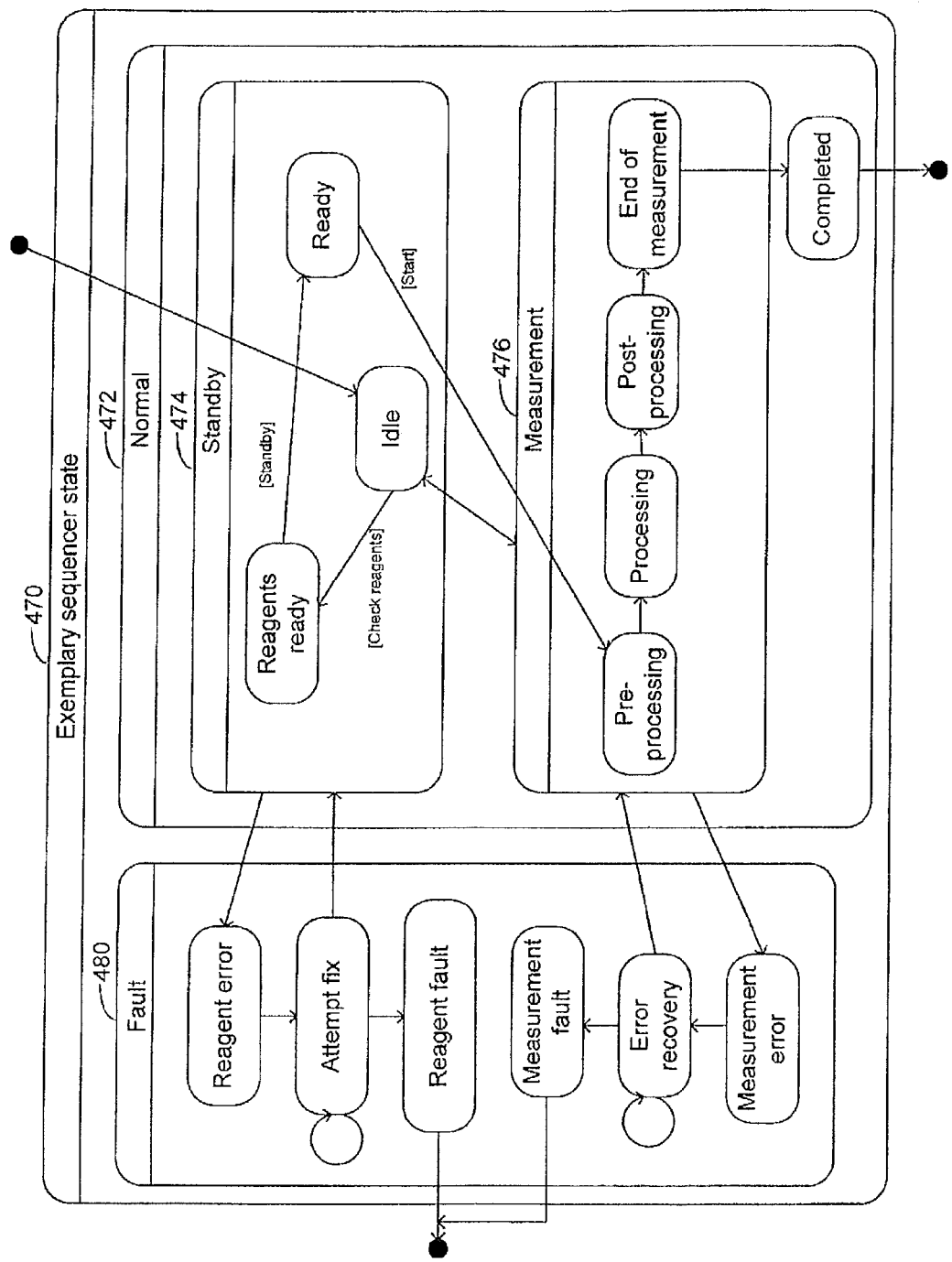

FIG. 8F illustrates a state 470 of the sequencer device. The device state 470 comprises a normal state 472 having a standby state 474 and a "measurement" state 476, and a fault state 480. For this device, reagents-readiness is selected to represent the various exemplary states in a manner similar to that described above in reference to FIG. 8B.

Figure 8G:
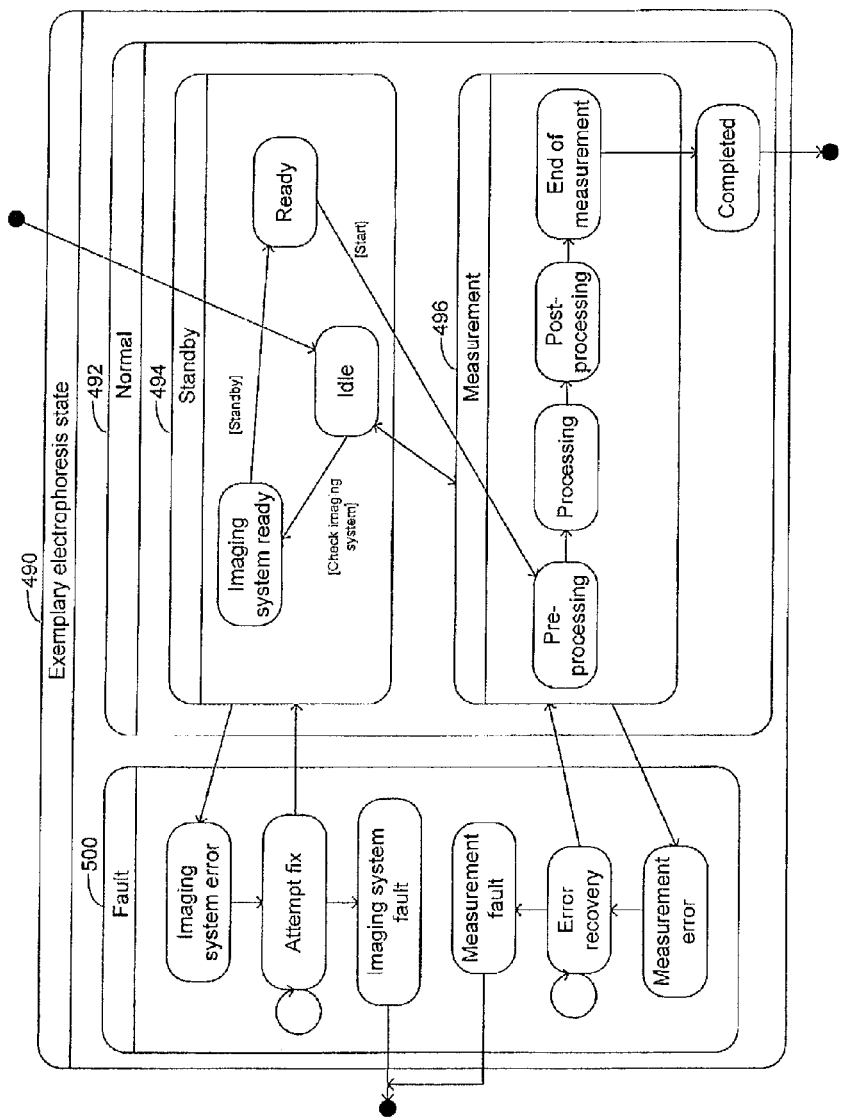

FIG. 8G illustrates a state 490 of the electrophoresis device. The device state 490 comprises a normal state 492 having a standby state 494 and a "measurement" state 496, and a fault state 500. For this device, an imaging system function is selected to represent the various exemplary states in a manner similar to that described above in reference to FIG. 8B.

Figure 8H:
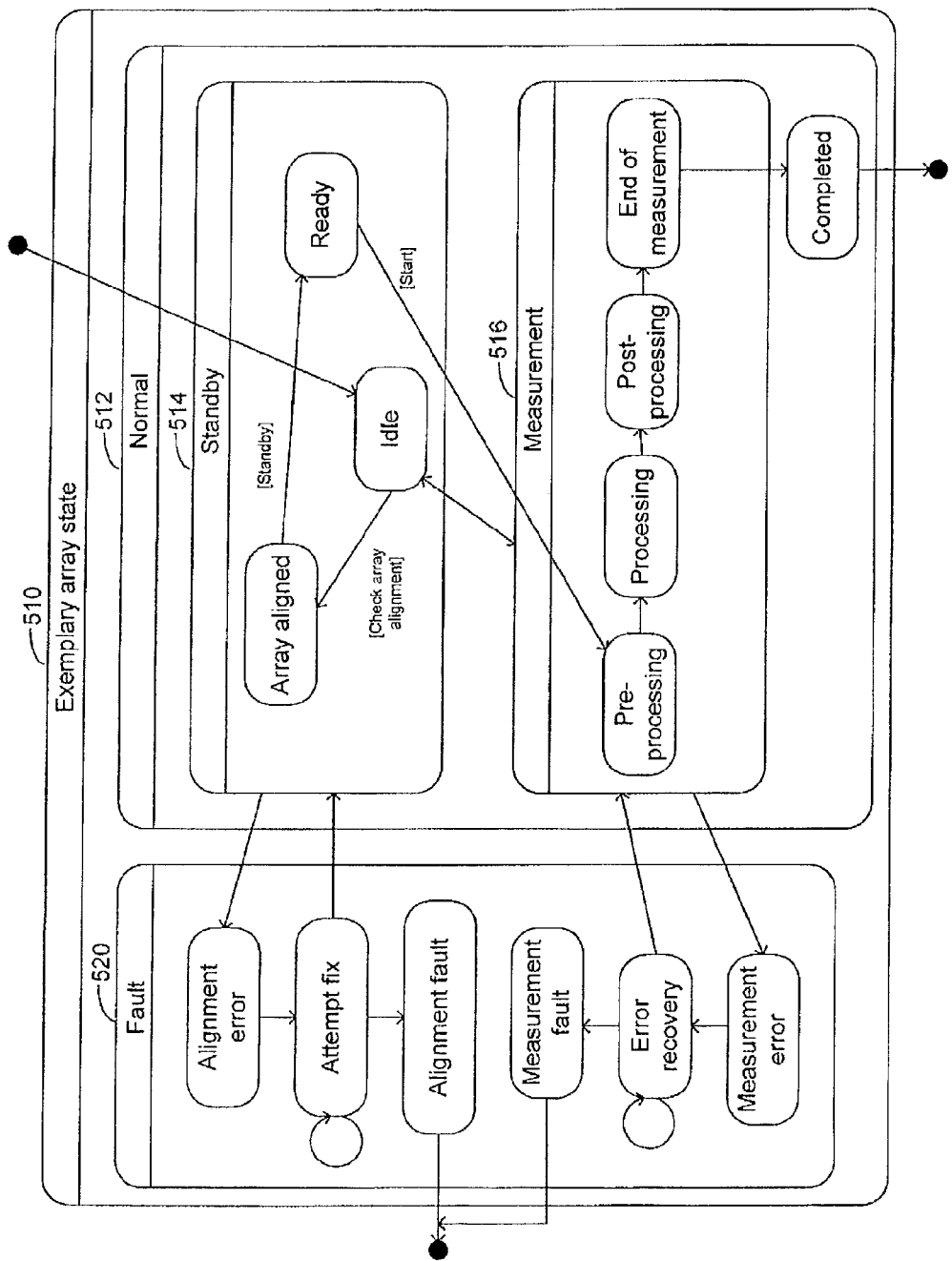

FIG. 8H illustrates a state 510 of the array device. The device state 510 comprises a normal state 512 having a standby state 514 and a "measurement" state 516, and a fault state 520. For this device, an alignment of the array is selected to represent the various exemplary states in a manner similar to that described above in reference to FIG. 8B.

Figure 8I:
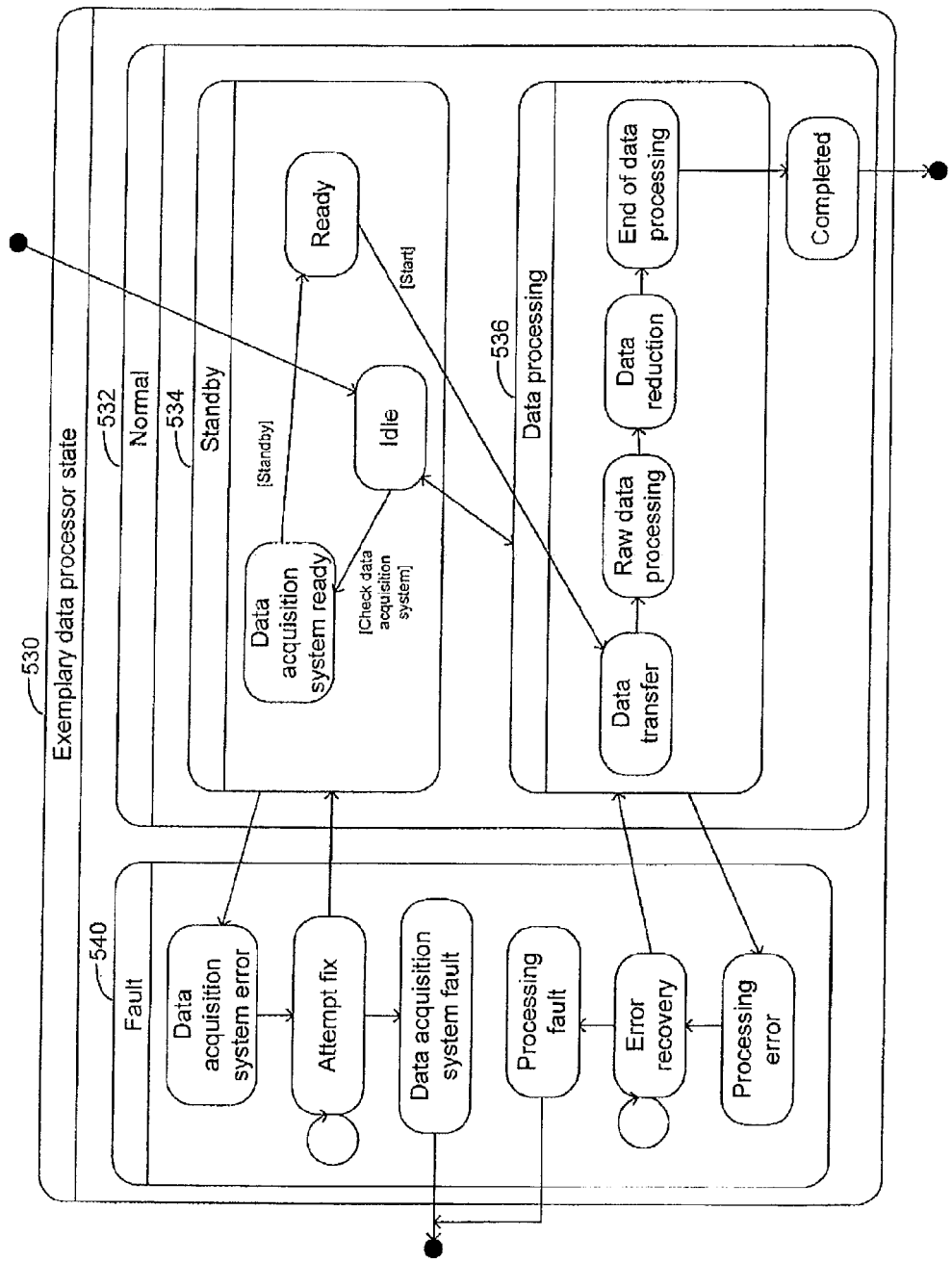

FIG. 8I illustrates a state 530 of the data processor device. The device state 530 comprises a normal state 532 having a standby state 534 and a "data processing" state 536, and a fault state 540. For this device, a data acquisition system readiness is selected to represent the various exemplary states in a manner similar to that described above in reference to FIG. 8B.

Figure 8J:
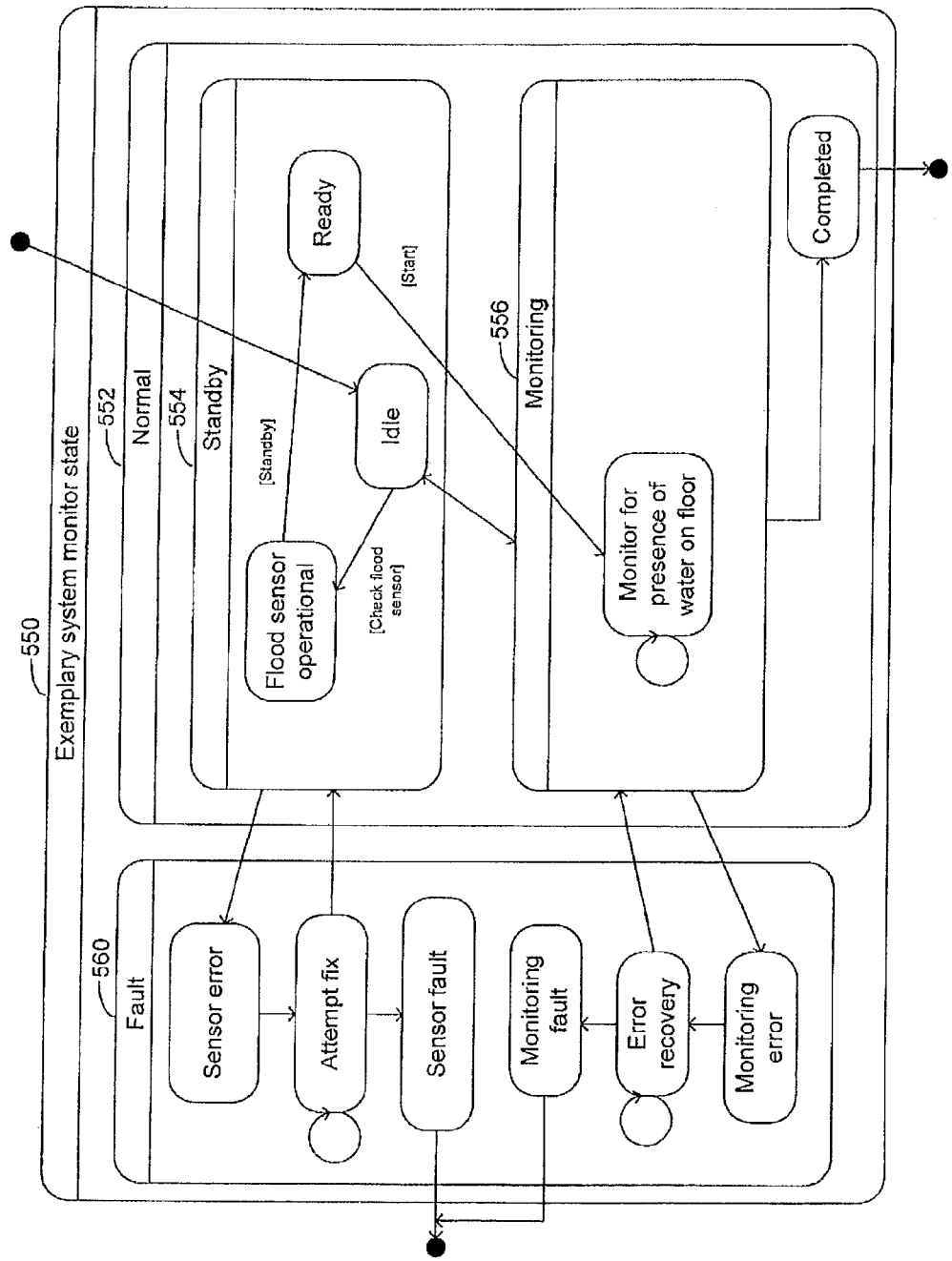

FIG. 8J illustrates a state 550 of the system monitor device. The device state 550 comprises a normal state 552 having a standby state 554 and a "monitoring" state 556, and a fault state 560. For this device, a water-detecting flood sensor function is selected to represent the various exemplary states in a manner similar to that described above in reference to FIG. 8B.

Figure 9A:
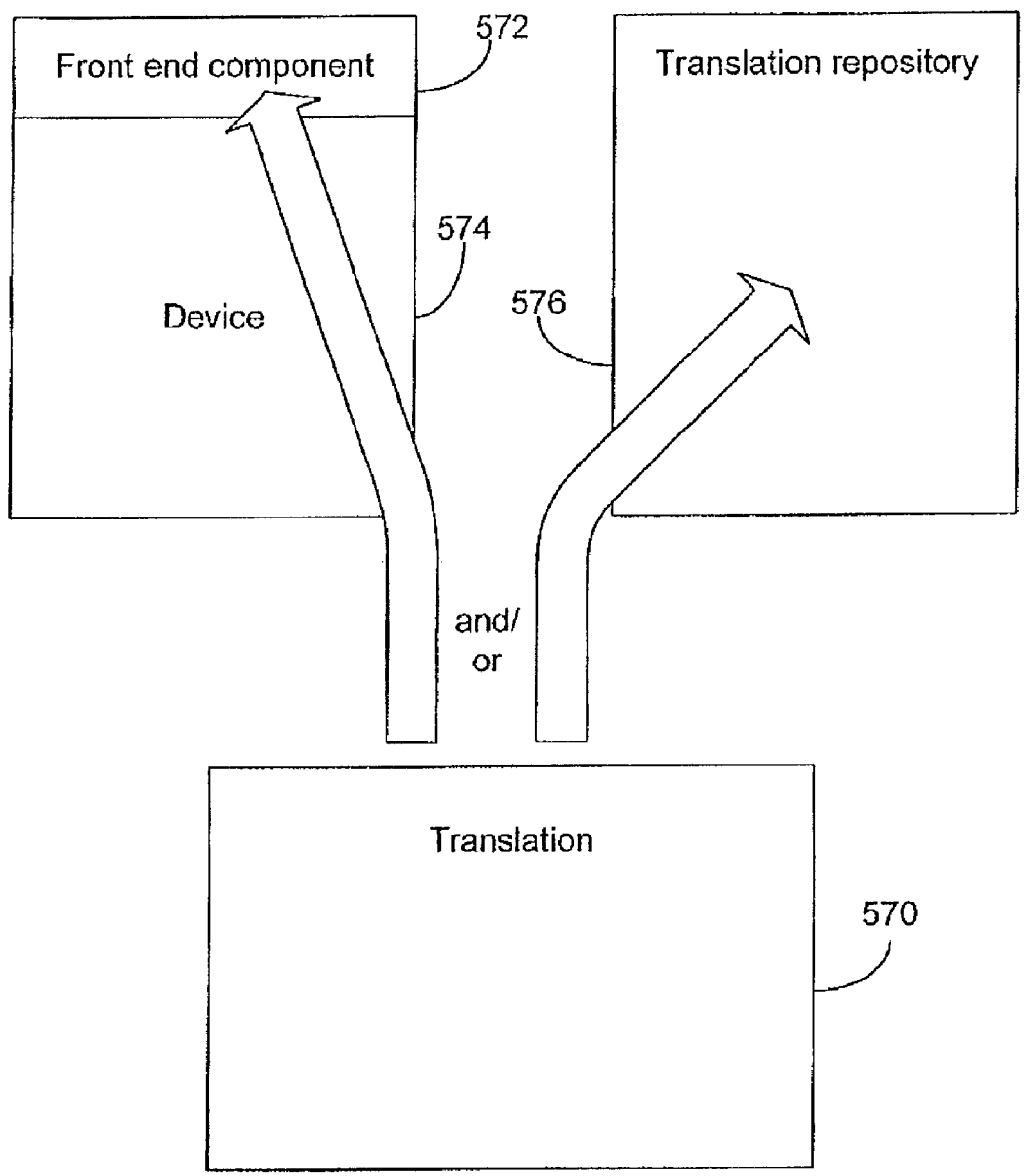
FIG. 9A illustrates how a translation entity may reside at various locations to act as the translator between the device and the control system.

In one aspect, the various device-specific states and commands that cause transitions between such states are monitored and coordinated by the previously described standardized formats of the states and commands. In FIGS. 1 and 8A, each of the various devices has associated with it some form of a translator. FIGS. 9A-B now illustrate how such translators may be implemented in a manner that provides the exemplary translation functionality as described above in reference to FIGS. 7A-C.

FIG. 9A illustrates a translation entity 570 that may reside in a front end component 572 of a device 574 and/or in a translation repository 576. It will be appreciated that the translation entity 570 may be in any number of locations, functional or physical, associated with the analytical system. It may reside within a front end module (FEM) of a device, in a computer physically proximate one or more of the devices, in a computer that hosts the control system, in a computer physically removed from the analytical system (but functionally connected), or in any other possible devices, memory units, processes, and the like.

FIG. 9B illustrates an exemplary. translation 580 that could be stored at any of the aforementioned locations and implemented to translate between a device and the control system. The translation 580 could be implemented in any number of ways, including but not limited to, a lookup table, an algorithm, and the like. The storage unit is used as an exemplary device for the purpose of describing the translation 580. Thus, the states illustrated in FIG. 8B are referred to in the description of the translation 580. It should be understood, however, that similar translation may be constructed for each of the devices in the analytical system. Furthermore, it will be appreciated that the logic of the exemplary translation 580 is only an example. Any other logics (and their implementations) that perform similar functions may be utilized without departing from the spirit of the present teachings.

The exemplary translation 580 can be generally divided into two groups for the purpose of forming a functional link between the control system and the device. The first group may include the translation of device-specific states to the STANDARDIZED states. The second group may include the translation of the STANDARDIZED commands to device-specific commands.

In the device-specific to STANDARDIZED state translation group, exemplary translations may be constructed as follows. If the unit is in any of the "idle," "nominal temperature," "ready," or "standby" states, then the translator outputs the STANDBY state to the control system. If the unit is in any of the "locate sample," "retrieve sample," "make sample accessible to robotics," "end of dispensing," or "dispensing" states, then the translator outputs the TASK state to the control system. If the unit is in any of the "non-nominal temperature," "attempt nominal temperature," "storage temperature fault," "dispensing error," "error recovery," "dispensing fault," or "fault" states, then the translator outputs the FAULT state to the control system. If the unit is in the "completed" state, then the translator outputs the COMPLETED state to the control system.

In the STANDARDIZED to device-specific command translation group, exemplary commands may be constructed as follows. If the control system issues the STANDBY command, the device is instructed to go into its standby state (via the idle state) if not in the standby state. If the device is already in the standby state, then the device is instructed to continue its standby operation.

If the control system issues the TASK command, the device is instructed to go into its dispensing state if not in the dispensing state. If the device is already in the dispensing state, then the device is instructed to continue its dispensing operation.

If the control system issues the FAULT command, it could be because the storage unit is at fault, or because another device(s) is at fault. If the storage unit is already in the fault state, then it is instructed to continue the fault handling process as described above in reference to FIG. 8B. If the unit is in the standby state, then it is instructed to remain in the standby state. If the unit is in the dispensing state, then it could be instructed to either to go into the standby state (while the other-device-caused fault is being worked on) if the fault affects the dispensing unit in some way, or to continue to dispense if the fault does not affect the dispensing unit. If the unit is in the completed state, then it could be instructed to ignore the FAULT command.

From the foregoing description, it should be apparent that by relegating the specifics of different devices to some form of translation entities and controlling the plurality of devices in a standardized format, the control system's ability to coordinate the activities of the devices is greatly simplified. As is known, the number of devices in many analytical systems may be relatively large to provide high throughput of sample analysis. The standardized coordination by a control system is particularly valuable in such large systems.

Figure 10A:
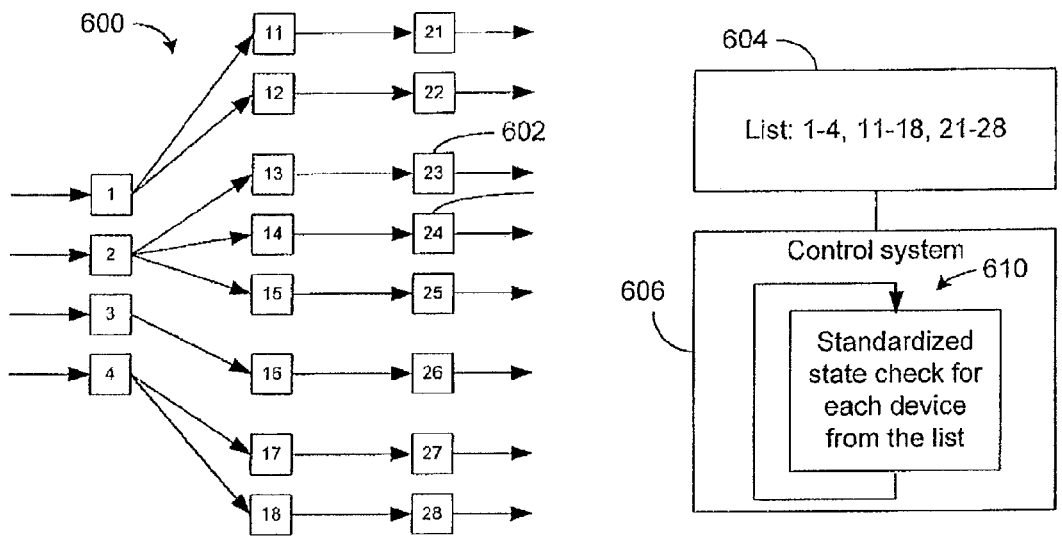
FIGS. 10A and 10B illustrate how the control system utilizing the standardized format facilitates configuring and coordinating large number of devices.
Figure 10B:
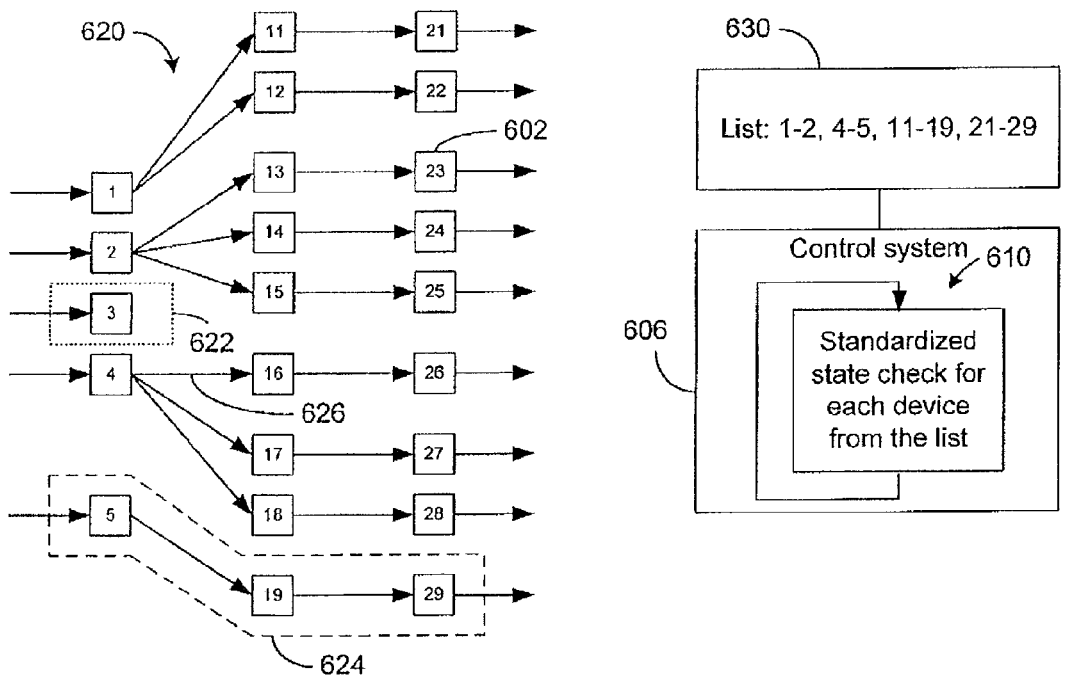

FIGS. 10A-B illustrate an exemplary change in the configuration of a portion of an analytic system. Such configuration change may be facilitated by the simple standardized treatment of the devices. FIG. 10A illustrates a first configuration 600 that comprises a plurality of devices 602 arranged in an exemplary manner as shown. A control system 610 coordinates the operation of the configuration 600 via a translation component 604. The translation component 604 comprises a list of devices in the configuration 600. The device-specific translators that correspond to the list of devices may reside in any of the locations described above.

FIG. 10B illustrates a second configuration 620 that results from some change in the physical and/or functional aspects of the first configuration 600. The exemplary changes are depicted as a removal of device labeled as "3" (indicated by box 622), reassignment of device "4" as the input for device "16" (indicated by arrow 626), and addition of a chain of devices "5," "19," and "29" (indicated by enclosed area 624). The control system 606 then adapts to the new configuration via a translation component 630 that has an updated list of devices.

In certain embodiments, the added device may be recognized as a known device by the control system or some other process that integrates the various devices of the analytical system. In such situations, the device integration may be performed without a tedious human intervention, by updating the device list and retrieving a known translation from some library of translations. In other embodiments, the added device may not be recognized by the control system. In such situations, the device integration may require an additional step of constructing a translation between the new device and the control system. Once such translation is constructed, the device behaves as one of the known devices, and can be coordinated along with the other devices in the analytical system.

Although the above-disclosed embodiments of the present invention have shown, described, and pointed out the fundamental novel features of the invention as applied to the above-disclosed embodiments, it should be understood that various omissions, substitutions, and changes in the form of the detail of the devices, systems, and/or methods illustrated may be made by those skilled in the art without departing from the scope of the present invention. Consequently, the scope of the invention should not be limited to the foregoing description, but should be defined by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

What is claimed is:

1. A system for coordinated communication and management of biological instrumentation, the system comprising:
    a client component configured to manage the operation of a plurality of biological analyzers, said client component comprising a state logic component configured to process operational state changes associated with a first biological analyzer and determine an associated operational state of a second biological analyzer such that the client component, in response to processing a state change from a first state to a second state associated with the first biological analyzer, determines a desired operational state of the second biological analyzer based upon the second state of the first biological analyzer and transmits instructions to the second biological analyzer to effectuate the desired operational state; and
    a plurality of analyzer components associated with the plurality of biological analyzers configured to receive said instructions from the client component and translate the instructions into commands capable of inducing the associated biological analyzer to achieve the desired operational state.

2. The system of claim 1, wherein the instructions transmitted by the client component are generic instructions that are translated by the analyzer components into specific commands capable of inducing the associated biological analyzer to achieve the desired operational state such that the state logic component can be updated to process operational state changes associated with new and existing biological analyzers without substantial modification of the generic instructions.

3. The system of claim 1, wherein the plurality of biological analyzers comprise applications configured to conduct biological data analysis.

4. The system of claim 1, wherein the plurality of biological analyzers comprise instruments configured to conduct biological data analysis.

5. The system of claim 4, wherein the plurality of biological analyzers comprise at least one instrument selected from the group consisting of: thermal cyclers, sequence detection instruments, mass spectrometers, and electrophoresis instruments.

6. The system of claim 1, wherein the plurality of biological analyzers comprise at least one robotic instrument configured to identify and physically manipulate at least one biological sample.

7. The system of claim 1, further comprising at least one directory configured to provide information to the client component as to logical location and parameters of said plurality of analyzer components such that the client component is able to manage the plurality of biological analyzers by referencing the information provided by the at least one directory to induce a selected biological analyzer to achieve the desired operational state.

8. The system of claim 7, further comprising at least one server component configured to provide data to the at least one directory that describes the operational parameters associated with the selected biological analyzer.

9. The system of claim 7, further comprising a messaging service that provides a mechanism for communication between the plurality of analyzer components and the client component such that a new biological analyzer can be configured for management by the client component by associating at least one of the analyzer components with said new biological analyzer and updating the at least one directory with information as to the logical location of the analyzer component allowing the client component to manage the operational state of the new biological analyzer using the operational parameters provided by the at least one directory.

10. The system of claim 1, wherein each of the plurality of analyzer components comprises application modules, including:
    a state model module configured to maintain the functional state of the biological analyzer within a corresponding state model, wherein the client component instructions effectuate transitions within the state model; and
    a translation module, which translates instructions received from the client component into operational commands recognized by the biological analyzer.

11. The system of claim 1, wherein at least a portion of the instructions effectuate changes between a normal operational state and a fault state for a selected biological analyzer.

12. The system of claim 11, wherein the normal operational state for the selected biological analyzer comprise a state selected from the group consisting of: task state, standby state, or completed state.

13. The system of claim 12, wherein the client component instructs the second biological analyzer to enter the task state when it is in the standby state awaiting the completion of the first biological analyzer and the client component determines the first biological analyzer has entered the completed state.

14. The system of claim 1, further comprising a system monitoring device that monitors the operating conditions of the plurality of biological analyzers.

15. A method for coordinated communication and management of biological instrumentation, the method comprising:
    monitoring generically represented operational states for a plurality of biological analyzers determined at least in part from analyzer-specific operational states associated with the biological analyzers wherein the analyzer-specific operational states are transformed into the generically represented operational states;
    determining at least one desired generically represented operational state for a first biological analyzer based upon a change in operational state of a second biological analyzer from a first generically represented operational state to a second generically represented operational state, wherein the determination is based at least in part on the monitored generically represented operational states for the plurality of biological analyzers; and transmitting generically represented operational commands to the plurality of biological analyzers, wherein the generically represented operational commands are transformed into analyzer-specific operational commands recognizable by the plurality of biological analyzers to thereby effectuate the achievement of the desired operational state in the first biological analyzer upon detection of a change in the operational state of the second biological analyzer from the first generically represented operational state to the second generically represented operational state.

16. The method of claim 15, wherein monitoring the generically represented operational states for the plurality of biological analyzers comprises determining when a selected biological analyzer is in a state selected from the group consisting of: a normal state, a fault state, a task state, a standby state, and a completed state.

17. The method of claim 15, wherein determining interrelated operational functioning for the plurality of biological analyzers comprises evaluating a current operational state for a first biological analyzer and in response, changing a second biological analyzer's operational state based at least in part upon the first biological analyzer's operational state.

18. The method of claim 17, wherein the second biological analyzer's operational state is changed to a task state from a standby state based upon the first biological analyzer's operational state being determined as a completed state.

19. The method of claim 15, wherein the generically represented operational commands transmitted to a selected biological analyzer are transformed by a front end component associated with the selected analyzer.

20. The method of claim 15, wherein the generically represented operational commands transmitted to a selected biological analyzer are transformed at a location other than at the selected analyzer.

21. The method of claim 15, wherein monitoring generically represented operational states for a plurality of biological analyzers comprises monitoring operational states for biological analyzers configured to analyze information selected from the group consisting of: nucleic acids, peptides, and proteins.

22. The method of claim 15, wherein monitoring generically represented operational states for a plurality of biological analyzers comprises monitoring operational states for biological analyzers selected from the group consisting of: thermal cyclers, sequence detection instruments, mass spectrometers and electrophoresis instruments.

23. The method of claim 15, wherein monitoring generically represented operational states and transmitting generically represented operational commands is facilitated by at least one directory configured to provide information about logical location and operational parameters associated with the plurality of biological analyzers, such that the monitoring or transmitting is achieved at least in part by referencing the information provided by the at least one directory to effectuate changes in the operational states for a selected biological analyzer.

24. The method of claim 23, wherein the at least one directory is associated with at least one server component configured for transmitting information of the at least one directory.

25. The method of claim 23, wherein a messaging service provides a mechanism for communicating with the plurality of biological analyzers.

* * * * *